US011806399B2

(12) United States Patent
Soane et al.

(10) Patent No.: US 11,806,399 B2
(45) Date of Patent: *Nov. 7, 2023

(54) EXCIPIENT COMPOUNDS FOR BIOPOLYMER FORMULATIONS

(71) Applicant: COMERA LIFE SCIENCES, INC., Woburn, MA (US)

(72) Inventors: David S. Soane, Palm Beach, FL (US); Philip Wuthrich, Watertown, MA (US); Rosa Casado Portilla, Middleton, MA (US); Robert P. Mahoney, Newbury, MA (US); Mark Moody, Concord, MA (US); Daniel G. Greene, Reading, MA (US)

(73) Assignee: COMERA LIFE SCIENCES, INC., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/175,162

(22) Filed: Feb. 12, 2021

(65) Prior Publication Data

US 2021/0162046 A1 Jun. 3, 2021

Related U.S. Application Data

(63) Continuation of application No. 16/659,046, filed on Oct. 21, 2019, which is a continuation of application No. 15/331,197, filed on Oct. 21, 2016, now Pat. No. 10,478,498, which is a continuation-in-part of application No. 14/966,549, filed on Dec. 11, 2015, now Pat. No. 9,605,051, which is a continuation of application No. 14/744,847, filed on Jun. 19, 2015, now abandoned.

(60) Provisional application No. 62/014,784, filed on Jun. 20, 2014, provisional application No. 62/083,623, filed on Nov. 24, 2014, provisional application No. 62/136,763, filed on Mar. 23, 2015, provisional application No. 62/245,513, filed on Oct. 23, 2015.

(51) Int. Cl.
| | |
|---|---|
| *A61K 39/395* | (2006.01) |
| *C07K 16/24* | (2006.01) |
| *C07K 16/32* | (2006.01) |
| *C07K 16/22* | (2006.01) |
| *A61K 47/22* | (2006.01) |
| *A61K 47/12* | (2006.01) |
| *A61K 47/02* | (2006.01) |
| *A61K 38/17* | (2006.01) |
| *A61K 47/20* | (2006.01) |
| *A61K 47/18* | (2017.01) |
| *A61K 47/42* | (2017.01) |
| *A61K 47/60* | (2017.01) |
| *C12N 9/36* | (2006.01) |
| *C12N 9/96* | (2006.01) |
| *A61K 38/19* | (2006.01) |
| *A61K 38/18* | (2006.01) |

(52) U.S. Cl.
CPC .... *A61K 39/39591* (2013.01); *A61K 38/1793* (2013.01); *A61K 38/1816* (2013.01); *A61K 38/193* (2013.01); *A61K 47/02* (2013.01); *A61K 47/12* (2013.01); *A61K 47/18* (2013.01); *A61K 47/20* (2013.01); *A61K 47/22* (2013.01); *A61K 47/42* (2013.01); *A61K 47/60* (2017.08); *C07K 16/22* (2013.01); *C07K 16/241* (2013.01); *C07K 16/32* (2013.01); *C12N 9/2462* (2013.01); *C12N 9/96* (2013.01); *C12Y 302/01017* (2013.01)

(58) Field of Classification Search
None
See application file for complete search history.

(56) References Cited

U.S. PATENT DOCUMENTS

| | | |
|---|---|---|
| 2,230,965 A | 2/1941 | Philip |
| 4,013,416 A | 3/1977 | Rittersdorf et al. |
| 4,548,827 A | 10/1985 | Katz et al. |
| 4,722,844 A | 2/1988 | Hattori et al. |
| 5,063,246 A | 11/1991 | Imai et al. |
| 5,164,214 A | 11/1992 | Wild et al. |
| 5,262,296 A | 11/1993 | Ogawa et al. |
| 5,608,038 A | 3/1997 | Eibl et al. |
| 5,849,700 A | 12/1998 | Soerensen et al. |
| 5,871,736 A | 2/1999 | Bruegger et al. |
| 5,900,416 A | 5/1999 | Markson |
| 6,013,773 A | 1/2000 | Kobayashi et al. |

(Continued)

FOREIGN PATENT DOCUMENTS

| | | |
|---|---|---|
| CA | 2951716 A1 | 12/2015 |
| CA | 3002373 A1 | 4/2017 |

(Continued)

OTHER PUBLICATIONS

Antihistamine, retrieved from the internet on Jun. 10, 2015. <http://faculty.weber.edu/ewalker/Medicinal_Chemistry/topicsAntihistam_local_anesth/antihista.htm>>. pp. 1-8.

(Continued)

*Primary Examiner* — Yunsoo Kim
(74) *Attorney, Agent, or Firm* — WILSON SONSINI GOODRICH & ROSATI

(57) ABSTRACT

The invention encompasses formulations and methods for the production thereof that permit the delivery of concentrated protein solutions. The inventive methods can yield a lower viscosity liquid protein formulation or a higher concentration of therapeutic or nontherapeutic proteins in the liquid formulation, as compared to traditional protein solutions. The inventive methods can also yield a higher stability of a liquid protein formulation.

25 Claims, 3 Drawing Sheets

(56) References Cited

U.S. PATENT DOCUMENTS

| | | | |
|---|---|---|---|
| 6,039,977 A | 3/2000 | Venkatraman et al. |
| 6,171,586 B1 | 1/2001 | Lam et al. |
| 6,267,958 B1 | 7/2001 | Andya et al. |
| 6,525,102 B1 | 2/2003 | Hora et al. |
| 6,685,940 B2 | 2/2004 | Andya et al. |
| 6,875,432 B2 | 4/2005 | Liu et al. |
| 7,390,786 B2 | 6/2008 | Warne et al. |
| 7,666,413 B2 | 2/2010 | Liu et al. |
| 7,758,860 B2 | 7/2010 | Warne et al. |
| 7,947,649 B2 | 5/2011 | Lopez et al. |
| 7,956,028 B2 | 6/2011 | Khanzada et al. |
| 7,964,561 B2 | 6/2011 | Garigapati et al. |
| 8,013,022 B2 | 9/2011 | Jones et al. |
| 8,039,633 B2 | 10/2011 | Nishimura et al. |
| 8,142,776 B2 | 3/2012 | Liu et al. |
| 8,318,161 B2 | 11/2012 | Esue et al. |
| 8,383,114 B2 | 2/2013 | Sloey et al. |
| 8,420,081 B2 | 4/2013 | Fraunhofer et al. |
| 8,440,184 B2 | 5/2013 | Georgiou et al. |
| 8,476,239 B2 | 7/2013 | Sunita et al. |
| 8,512,754 B2 | 8/2013 | Needham |
| 8,568,720 B2 | 10/2013 | Kameoka et al. |
| 8,613,919 B1 | 12/2013 | Ma et al. |
| 8,617,568 B2 | 12/2013 | Rhee et al. |
| 8,633,034 B2 | 1/2014 | Trotter et al. |
| 8,679,479 B2 | 3/2014 | Georgiou et al. |
| 8,703,126 B2 | 4/2014 | Shire et al. |
| 8,715,652 B2 | 5/2014 | Styger et al. |
| 8,802,603 B2 | 8/2014 | D'Souza et al. |
| 8,961,964 B2 | 2/2015 | Shire et al. |
| 9,339,545 B2 | 5/2016 | Prestrelski et al. |
| 9,352,043 B2 | 5/2016 | Osslund |
| 9,605,051 B2 * | 3/2017 | Soane .......... A61K 39/395 |
| 9,649,364 B2 | 5/2017 | Prestrelski et al. |
| 9,795,674 B2 | 10/2017 | Parshad et al. |
| 9,867,881 B2 * | 1/2018 | Soane .......... A61K 39/395 |
| 9,943,601 B2 | 4/2018 | Manning et al. |
| 10,000,562 B2 | 6/2018 | Deshmukh et al. |
| 10,206,924 B2 | 2/2019 | Whitehead et al. |
| 10,279,048 B2 | 5/2019 | Soane et al. |
| 10,478,498 B2 * | 11/2019 | Soane .......... A61K 47/60 |
| 10,646,569 B2 | 5/2020 | Shenoy |
| 11,357,857 B2 | 6/2022 | Soane et al. |
| 11,660,343 B2 | 5/2023 | Soane et al. |
| 2002/0045571 A1 | 4/2002 | Liu et al. |
| 2003/0092607 A1 | 5/2003 | Carpenter et al. |
| 2003/0113316 A1 | 6/2003 | Kaisheva et al. |
| 2003/0138417 A1 | 7/2003 | Kaisheva et al. |
| 2003/0202972 A1 | 10/2003 | Andya et al. |
| 2004/0071988 A1 | 4/2004 | Nawrocki et al. |
| 2004/0081702 A1 | 4/2004 | Kim et al. |
| 2004/0191243 A1 | 9/2004 | Chen et al. |
| 2004/0197324 A1 | 10/2004 | Liu et al. |
| 2005/0158303 A1 | 7/2005 | Liu et al. |
| 2005/0175603 A1 | 8/2005 | Liu et al. |
| 2006/0182740 A1 | 8/2006 | Yang et al. |
| 2006/0216377 A1 | 9/2006 | Milon et al. |
| 2006/0281931 A1 | 12/2006 | Leinweber et al. |
| 2007/0053900 A1 | 3/2007 | Liu et al. |
| 2007/0086995 A1 | 4/2007 | Liu et al. |
| 2007/0116700 A1 | 5/2007 | Liu et al. |
| 2008/0071063 A1 | 3/2008 | Allan et al. |
| 2008/0287417 A1 | 11/2008 | Ebner et al. |
| 2009/0035275 A1 | 2/2009 | Pickering et al. |
| 2009/0047328 A1 | 2/2009 | Cunningham |
| 2009/0280129 A1 | 11/2009 | Liu et al. |
| 2009/0291062 A1 | 11/2009 | Fraunhofer et al. |
| 2010/0044268 A1 | 2/2010 | Hormes et al. |
| 2010/0239567 A1 | 9/2010 | Esue et al. |
| 2010/0297106 A1 | 11/2010 | Sloey et al. |
| 2011/0046052 A1 | 2/2011 | Yang et al. |
| 2011/0066111 A1 | 3/2011 | Teschner et al. |
| 2011/0106044 A1 | 5/2011 | Trotter et al. |
| 2011/0112029 A1 | 5/2011 | Nielsen et al. |
| 2012/0076783 A1 | 3/2012 | Liu et al. |
| 2012/0082715 A1 | 4/2012 | Needham et al. |
| 2012/0184489 A1 | 7/2012 | Rau et al. |
| 2013/0058958 A1 | 3/2013 | Bowen et al. |
| 2013/0071411 A1 | 3/2013 | Boudreault et al. |
| 2013/0102760 A1 | 4/2013 | Bolli et al. |
| 2013/0149335 A1 | 6/2013 | Jezek et al. |
| 2013/0171128 A1 | 7/2013 | Huang et al. |
| 2013/0216525 A1 | 8/2013 | Chen et al. |
| 2013/0224213 A1 | 8/2013 | Esue et al. |
| 2013/0309226 A1 | 11/2013 | Armstrong et al. |
| 2014/0055254 A1 | 2/2014 | Adams |
| 2014/0057861 A1 | 2/2014 | Yan et al. |
| 2014/0065159 A1 | 3/2014 | Ma et al. |
| 2014/0072559 A1 | 3/2014 | Soula et al. |
| 2014/0105909 A1 | 4/2014 | Clogston et al. |
| 2014/0255423 A1 | 9/2014 | Hickman et al. |
| 2014/0342006 A1 | 11/2014 | Li |
| 2014/0378655 A1 | 12/2014 | Anderson |
| 2015/0007187 A1 | 1/2015 | Shows |
| 2015/0044198 A1 | 2/2015 | Shire et al. |
| 2015/0071879 A1 | 3/2015 | Jezek |
| 2015/0071920 A1 | 3/2015 | Langer et al. |
| 2015/0071921 A1 | 3/2015 | Langer et al. |
| 2015/0071922 A1 | 3/2015 | Langer et al. |
| 2015/0071925 A1 | 3/2015 | Larson et al. |
| 2015/0148526 A1 | 5/2015 | Gagnon |
| 2015/0225485 A1 | 8/2015 | Liu et al. |
| 2015/0313996 A1 | 11/2015 | Park et al. |
| 2015/0342968 A1 | 12/2015 | Mondragn et al. |
| 2016/0010063 A1 | 1/2016 | Selvitelli et al. |
| 2016/0068609 A1 | 3/2016 | Goletz et al. |
| 2016/0074515 A1 | 3/2016 | Soane et al. |
| 2016/0096879 A1 | 4/2016 | Soane et al. |
| 2016/0271253 A1 | 9/2016 | Chang |
| 2017/0087215 A1 | 3/2017 | Prestrelski et al. |
| 2017/0157256 A1 | 6/2017 | Soane et al. |
| 2017/0232103 A1 | 8/2017 | Soane et al. |
| 2018/0015168 A1 | 1/2018 | Soane et al. |
| 2018/0333493 A1 | 11/2018 | Shenoi |
| 2019/0054175 A1 | 2/2019 | Soane et al. |
| 2020/0114002 A1 | 4/2020 | Soane et al. |
| 2020/0316196 A1 | 10/2020 | Soane et al. |
| 2021/0113697 A1 | 4/2021 | Soane et al. |
| 2023/0027396 A1 | 1/2023 | Soane et al. |
| 2023/0028812 A1 | 1/2023 | Soane et al. |

FOREIGN PATENT DOCUMENTS

| | | |
|---|---|---|
| CN | 101378773 A | 3/2009 |
| CN | 101442915 A | 5/2009 |
| CN | 102946903 A | 2/2013 |
| CN | 106535918 A | 3/2017 |
| JP | 2012170366 A | 9/2012 |
| JP | 2015522019 A | 8/2015 |
| JP | 2016534141 A | 11/2016 |
| KR | 20060017583 A | 2/2006 |
| KR | 20120130757 A | 12/2012 |
| WO | WO-9727750 A1 | 8/1997 |
| WO | 2004037018 A1 | 5/2004 |
| WO | 2004084875 A1 | 10/2004 |
| WO | 2004091658 A1 | 10/2004 |
| WO | 2006119054 A2 | 11/2006 |
| WO | 2007106731 A2 | 9/2007 |
| WO | 2011109415 A2 | 9/2011 |
| WO | 2011139718 A1 | 11/2011 |
| WO | 2014037680 A1 | 3/2014 |
| WO | 2015038818 A2 | 3/2015 |
| WO | WO-2015196091 A1 | 12/2015 |
| WO | WO-2015196187 A1 | 12/2015 |
| WO | 2016054259 A1 | 4/2016 |
| WO | WO-2017070501 A1 | 4/2017 |
| WO | WO-2018013673 A1 | 1/2018 |
| WO | WO-2018152165 A1 | 8/2018 |
| WO | WO-2019036619 A1 | 2/2019 |
| WO | WO-2019173338 A1 | 9/2019 |
| WO | 2020112855 A1 | 6/2020 |
| WO | WO-2021072050 A1 | 4/2021 |
| WO | WO-2021108427 A1 | 6/2021 |
| WO | WO-2022056220 A2 | 3/2022 |

(56) References Cited

FOREIGN PATENT DOCUMENTS

OTHER PUBLICATIONS

Local Anesthetics handout, retrieved from the Internet on Oct. 15, 2015. <<http://www.medbox.org/surgeryanaesthesia/local-anesthesia-handout/preview?q=>>. International federation of nurse anesthetics, 2014.
"Aeglea Biotherapeutics Raises $44 Million in Series B Financing", Mar. 23, 2015 Press Release, retrieved from the internet <http://ir.aegleabio.com/phoenix.zhtml?c=254096&p=irol-newsArticle&ID=2069753>>.
"GNPD-Coffee Drink", Retrieved from the Internet: URL:http://www.gnpd.com/sinatra/recordpage/10245855/from_search/flEWaYhnVb/?page=l [retrieved on Nov. 9, 2017].
Becker, D. E. et al., "Essentials of Local Anesthetic Pharmacology", Anesth Prog, 53, 2006, 98-109.
Becker, D. E. et al., "Local Anesthetics: Review of Pharmacological Considerations", Anesth Prog., 59, 2012, 90-102.
Connolly, B. D. et al., "Weak Interactions Govern the Viscosity of Concentrated Antibody Solutions: High-Throughput Analysis Using the Diffusion Interaction Parameter", Biophysical Journal, 103(1), Jul. 2012, 69-78.
Davidson, P. et al., "Effect of Sucrose/Raffinose Mass Ratios on the Stability of Co-Pyophilized Protein During Storage above the Tg", Pharmaceutical Research, vol. 18, 2001, 474-479.
Du, W. et al., "Hydrophobic Salts Markedly Diminish Viscosity of Concentrated Protein Solutions", Biotechnol. Bioeng., 108(3), Mar. 2011, 632-636.
Glazer, E. S. et al., "Bioengineered Human Arginase I with Enhanced Activity and Stability Controls Hepatocellular and Pancreatic Carcinoma Xenografts", Translational Oncology, 4(3), 2011, 138-146.
Guo, Z. et al., "Structure-Activity Relationship for Hydrophobic Salts as Viscosity-Lowering Excipients for Concentrated Solutions of Monoclonal Antibodies", Pharm Res., 29, 2012, 3102-3109.
Hung, J. J. et al., "High Concentration Tangential Flow Ultrafiltration of Stable Monoclonal Antibody Solutions with Low Viscosities", Manuscript available via Elsevier.com, 2016.
Liu, J. et al., "Reversible self-association increases the viscosity of a concentrated monoclonal antibody in aqueous solution", J. Pharm. Sci., 94(9), Sep. 30, 2005, 1928-1940.
Shi, et al., "Method qualification and application of diffusion interaction parameter and virial coefficient", International Journal of Biological Macromolecules, 62, 2013, 487-493.
Stone, E. et al., "Strategies for optimizing the serum persistence of engineered human arginase I for cancer therapy", J. of Controlled Release, 158, 2012, 171-179.
Stone, E. M. et al., "Replacing Mn2+ with Co2+ in Human Arginase I Enhances Cytotoxicity toward L-Arginine Auxotrophic Cancer Cell Lines", ACS Chemical Biology, 5(3), 2010, 333-342.
Tomar, D. S. et al., "Molecular basis of high viscosity in concentrated antibody solutions: Strategies for high concentration drug product development", MABS, 8(2), 2016, 216-228.
Weight, A. K. "Enhancing pharmaceutical formulations to improve efficacy and delivery of drug molecules", paper submitted at the Massachusetts Institute of Technology, Jun. 2013, 1-93.
Xu, Shuyun et al., Clinical Pharmacology, vol. Two, published in Hefei by Anhui Science & Technology Press, Edition 1, Jul. 31, 1981, 711-712.
Yadav, S. et al., "Specific interactions in high concentration antibody solutions resulting high viscosity", J. Pharm. Sci., 99(3), Mar. 31, 2010, 1152-1158.
Chapter 1, Section II(F) of book titled "Caffeine" CRC press 1998, edited by Gene Spiller, ISBN 0-8493-2647-8.
http://www.inchem.org/documents/icsc/icsc/eics0405.htm.
https://pubchem.ncbi.nlm.nih.gov/compound/Caffeine; pp. 1-211.
Boob, M. et al., "TMAO: Protecting Proteins from Feeling the Heat", Retrieved from the internet on Jan. 18, 2022, URL: https://chemrxiv.org/engage/api-gateway/chemrxiv/assets/orp/resource/item/60c74ddf337d6cab37e27e8a/original/tmao-protecting-proteins-from-feeling-the-heat.pdf, Jul. 17, 2020, 1-15.
Jezek, J. et al., "Viscosity of Concentrated Therapeutic Protein Compositions", Adv. Drug Deliv. Rev., 63(13), https://doi.org/10.1016/j.addr.2011.09.008, Oct. 2011, 1107-1117.
Johnson, Jr., W. "Safety Assessment of Ascorbyl Glucoside and Sodium Ascrbyly Glucoside as Used in Cosmetics", Retrieved from the internet on Jan. 18, 2022, URL: https://www.cir-safety.org/sites/default/files/Ascorbyl%20Glucoside_1.pdf, Aug. 21, 2020, 1-37.
Ratanji, K. D. et al., "Immunogenicity of therapeutic proteins: Influence of aggregation", J Immunotoxicol., 11(2), (doi: 10.3109/1547691X.2013.821564), 2014, 99-109.
Worland, J. "Why Some Experts Want Mandatory Flu Shots for School Kids", Published Jan. 7, 2015 (Jan. 7, 2015). Retrieved Oct. 2018 (Oct. 4, 2018) (http://time.com/3657461/mandatory-flu-shots/)pp. 1-3.
Jiskoot W, et al., "Ongoing Challenges to Develop High Concentration Monoclonal Antibody-based Formulations for Subcutaneous Administration: Quo Vadis?" J Pharm Sci. Apr. 2022;111(4):861-867. Epub Nov. 20, 2021.
Krayukhina, E. et al., "Effects of Syringe Material and Silicone Oil Lubrication on the Stability of Pharmaceutical Proteins", Journal of Pharmaceutical Sciences, 104, 2015, 527-535.
PCT/US2016/058169 International Search Report and Written Opinion dated Feb. 16, 2017.
PCT/US2022/049799 International Search Report and Written Opinion dated Apr. 26, 2023.
Sei, M. , et al., "Advances in Biopharmaceutical and Vaccine Manufacturing Plants", Hitachi Critique, 94(12), 2013, 848-851.
Strickley, RG., et al., "A review of Formulations of Commercially Available Antibodies." J Pharm Sci. Jul. 2021;110(7):2590-2608.e56. Epub Mar. 28, 2021.
Thurow, H. et al., "Stabilisation of Dissolved Proteins Against Denaturation at Hydrophobic Interfaces", Diabetologia, 27, 1984, 212-218.

* cited by examiner

EXCIPIENT COMPOUNDS FOR BIOPOLYMER FORMULATIONS

RELATED APPLICATIONS

This application is a continuation of U.S. application Ser. No. 16/659,046 filed Oct. 21, 2019, which is a continuation of U.S. application Ser. No. 15/331,197 filed Oct. 21, 2016 (now U.S. Pat. No. 10,478,498), which is a continuation-in-part of U.S. application Ser. No. 14/966,549 filed Dec. 11, 2015 (now U.S. Pat. No. 9,605,051), which is a continuation of U.S. application Ser. No. 14/744,847 filed Jun. 19, 2015, which claims the benefit of U.S. Provisional Application No. 62/014,784 filed Jun. 20, 2014, U.S. Provisional Application No. 62/083,623, filed Nov. 24, 2014, and U.S. Provisional Application Ser. No. 62/136,763 filed Mar. 23, 2015; U.S. application Ser. No. 14/966,549 know U.S. Pat. No. 9,605, 051), also claims the benefit of U.S. Provisional Application No. 62/245,513, filed Oct. 23, 2015; U.S. application Ser. No. 15/331,197 filed Oct. 21, 2016 also claims the benefit of U.S. Provisional Application No. 62/245,513, filed Oct. 23, 2015. The entire contents of the each of the above applications are incorporated by reference herein.

FIELD OF APPLICATION

This application relates generally to formulations for delivering biopolymers.

BACKGROUND

Biopolymers may be used for therapeutic or non-therapeutic purposes. Biopolymer-based therapeutics, such as antibody or enzyme formulations, are widely used in treating disease. Non-therapeutic biopolymers, such as enzymes, peptides, and structural proteins, have utility in non-therapeutic applications such as household, nutrition, commercial, and industrial uses.

Biopolymers used in therapeutic applications must be formulated to permit their introduction into the body for treatment of disease. For example, it is advantageous to deliver 30 antibody and protein/peptide biopolymer formulations by subcutaneous (SC) or intramuscular (IM) routes under certain circumstances, instead of administering these formulations by intravenous (IV) injections. In order to achieve better patient compliance and comfort with SC or IM injection though, the liquid volume in the syringe is typically limited to 2 to 3 ccs and the viscosity of the formulation is typically lower than about 20 centipoise (cP) so that the formulation can be delivered using conventional medical devices and small-bore needles. These delivery parameters do not always fit well with the dosage requirements for the formulations being delivered.

Antibodies, for example, may need to be delivered at high dose levels to exert their intended therapeutic effect. Using a restricted liquid volume to deliver a high dose level of an antibody formulation can require a high concentration of the antibody in the delivery vehicle, sometimes exceeding a level of 150 mg/mL. At this dosage level, the viscosity-versus-concentration plots of the formulations lie beyond their linear-nonlinear transition, such that the viscosity of the formulation rises dramatically with increasing concentration. Increased viscosity, however, is not compatible with standard SC or IM delivery systems.

As an additional concern, solutions of biopolymer-based therapeutics are also prone to stability problems, such as precipitation, fragmentation, oxidation, deamidation, hazing, opalescence, denaturing, and gel formation, reversible or irreversible aggregation. The stability problems limit the shelf life of the solutions or require special handling.

As an example, one approach to producing protein formulations for injection is to transform the therapeutic protein solution into a powder that can be reconstituted to form a suspension suitable for SC or IM delivery. Lyophilization is a standard technique to produce protein powders. Freeze-drying, spray drying and even precipitation followed by super-critical-fluid extraction have been used to generate protein powders for subsequent reconstitution. Powdered suspensions are low in viscosity before re-dissolution (compared to solutions at the same overall dose) and thus may be suitable for SC or IM injection, provided the particles are sufficiently small to fit through the needle. However, protein crystals that are present in the powder have the inherent risk of triggering immune response. The uncertain protein stability/activity following re-dissolution poses further concerns. There remains a need in the art for techniques to produce low viscosity protein formulations for therapeutic purposes while avoiding the limitations introduced by protein powder suspensions.

In addition to the therapeutic applications of proteins described above, biopolymers such as enzymes, peptides, and structural proteins can be used in non-therapeutic applications. These non-therapeutic biopolymers can be produced from a number of different pathways, for example, derived from plant sources, animal sources, or produced from cell cultures.

The non-therapeutic proteins can be produced, transported, stored, and handled as a granular or powdered material or as a solution or dispersion, usually in water. The biopolymers for non-therapeutic applications can be globular or fibrous proteins, and certain forms of these materials can have limited solubility in water or exhibit high viscosity upon dissolution. These solution properties can present challenges to the formulation, handling, storage, pumping, and performance of the non-therapeutic materials, so there is a need for methods to reduce viscosity and improve solubility and stability of non-therapeutic protein solutions.

Proteins are complex biopolymers, each with a uniquely folded 3-D structure and surface energy map (hydrophobic/hydrophilic regions and charges). In concentrated protein solutions, these macromolecules may strongly interact and even inter-lock in complicated ways, depending on their exact shape and surface energy distribution. "Hot-spots" for strong specific interactions lead to protein clustering, increasing solution viscosity. To address these concerns, a number of excipient compounds are used in biotherapeutic formulations, aiming to reduce solution viscosity by impeding localized interactions and clustering. These efforts are individually tailored, often empirically, sometimes guided by in silico simulations. Combinations of excipient compounds may be provided, but optimizing such combinations again must progress empirically and on a case-by case basis.

There remains a need in the art for a truly universal approach to reducing viscosity in protein formulations at a given concentration under nonlinear conditions. There is an additional need in the art to achieve this viscosity reduction while preserving the activity of the protein and avoiding stability problems. It would be further desirable to adapt the viscosity-reduction system to use with formulations having tunable and sustained release profiles, and to use with formulations adapted for depot injection.

SUMMARY OF THE INVENTION

Disclosed herein, in embodiments, are liquid formulations comprising a protein and an excipient compound selected from the group consisting of hindered amine compounds, aromatic compounds, functionalized amino acids, oligopeptides, short-chain organic acids, low molecular weight aliphatic polyacids, and sulfones, wherein the excipient compound is added in a viscosity-reducing amount. In embodiments, the protein is a PEGylated protein and the excipient is a low molecular weight aliphatic polyacid. In embodiments, the excipient compound is an aromatic compound, and the aromatic compound can be a phenol or a polyphenol. In embodiments, the protein is a PEGylated protein. In embodiments, the formulation is a pharmaceutical composition, and the pharmaceutical composition comprises a therapeutic protein, wherein the excipient compound is a pharmaceutically acceptable excipient compound. In embodiments, the formulation is a non-therapeutic formulation, and the non-therapeutic formulation comprises a non-therapeutic protein. In embodiments, the therapeutic protein is selected from the group consisting of bevacizumab, trastuzumab, adalimumab, infliximab, etanercept, darbepoetin alfa, epoetin alfa, cetuximab, pegfilgrastim, filgrastim, and rituximab. In embodiments, the excipient compound is formulated as a concentrated excipient solution. In embodiments, the viscosity-reducing amount reduces viscosity of the formulation to a viscosity less than the viscosity of a control formulation. In embodiments, the viscosity of the formulation is at least about 10% less than the viscosity of the control formulation, or is at least about 30% less than the viscosity of the control formulation, or is at least about 50% less than the viscosity of the control formulation, or is at least about 70% less than the viscosity of the control formulation, or is at least about 90% less than the viscosity of the control formulation. In embodiments, the viscosity is less than about 100 cP, or is less than about 50 cP, or is less than about 20 cP, or is less than about 10 cP. In embodiments, the excipient compound has a molecular weight of <5000 Da, or <1500 Da, or <500 Da. In embodiments, the formulation contains at least about 1 mg/ml of the protein, or at least about 25 mg/mL of the protein, or at least about 50 mg/mL of the protein, or at least about 100 mg/mL of the protein, or at least about 200 mg/mL of the protein. In embodiments, the formulation comprises between about 0.001 mg/mL to about 60 mg/mL of the excipient compound, or comprises between about 0.1 mg/mL to about 50 mg/mL of the excipient compound, or comprises between about 1 mg/mL to about 40 mg/mL, or comprises between about 5 mg/mL to about 30 mg/mL of the excipient compound. In embodiments, the formulation has an improved stability when compared to the control formulation. The improved stability can be manifested as a decrease in the formation of visible particles, subvisible particles, aggregates, turbidity, opalescence, or gel. In embodiments, the formulation has an improved stability, wherein the improved stability is determined by comparison with a control formulation, and wherein the control formulation does not contain the excipient compound. In embodiments, the improved stability prevents an increase in particle size as measured by light scattering. In embodiments, the improved stability is manifested by a percent monomer that is higher than the percent monomer in the control formulation, wherein the percent monomer is measured by size exclusion chromatography. In embodiments, the excipient compound is a hindered amine, which can be caffeine. In embodiments, the hindered amine is selected from the group consisting of caffeine, theophylline, tyramine, imidazole, aspartame, saccharin, acesulfame potassium, pyrimidinone, 1,3-dimethyluracil, triaminopyrimidine, pyrimidine, and theacrine. In embodiments, the hindered amine is caffeine. In embodiments, the formulation can comprise an additional agent selected from the group consisting of preservatives, surfactants, sugars, polysaccharides, arginine, proline, hyaluronidase, stabilizers, solubilizers, co-solvents, hydrotropes, and buffers.

Further disclosed herein are methods of treating a disease or disorder in a mammal in need thereof, comprising administering to said mammal a liquid therapeutic formulation, wherein the therapeutic formulation comprises a therapeutically effective amount of a therapeutic protein, and wherein the formulation further comprises an pharmaceutically acceptable excipient compound selected from the group consisting of hindered amine compounds, aromatic compounds, functionalized amino acids, oligopeptides, short-chain organic acids, low molecular weight aliphatic polyacids, and sulfones; and wherein the therapeutic formulation is effective for the treatment of the disease or disorder. In embodiments, the therapeutic protein is a PEGylated protein, and the excipient compound is a low molecular weight aliphatic polyacid. In embodiments, the therapeutic protein is a PEGylated protein, and the excipient compound is an aromatic compound, which can be a phenol or a polyphenol, and the polyphenol can be tannic acid. In embodiments, the excipient is a hindered amine. In embodiments, the formulation is administered by subcutaneous injection, or an intramuscular injection, or an intravenous injection. In embodiments, the excipient compound is present in the therapeutic formulation in a viscosity-reducing amount, and the viscosity-reducing amount reduces viscosity of the therapeutic formulation to a viscosity less than the viscosity of a control formulation. In embodiments, the excipient compound is prepared as a concentrated excipient solution. In embodiments, the therapeutic formulation has an improved stability when compared to the control formulation. In embodiments, the excipient compound is essentially pure. Disclosed herein, in embodiments, are methods of improving stability of a liquid protein formulation, comprising: preparing a liquid protein formulation comprising a therapeutic protein and an excipient compound selected from the group selected from the group consisting of hindered amine compounds, aromatic compounds, functionalized amino acids, oligopeptides, short-chain organic acids, low molecular weight aliphatic polyacids, and sulfones, wherein the liquid protein formulation demonstrates improved stability compared to a control liquid protein formulation, wherein the control liquid protein formulation does not contain the excipient compound and is otherwise substantially similar to the liquid protein formulation. In embodiments, the excipient compound is formulated as a concentrated excipient solution. The stability of the liquid formulation can be a chemical stability manifested by resistance to a chemical reaction selected from the group consisting of hydrolysis, photolysis, oxidation, reduction, deamidation, disulfide scrambling, fragmentation, and dissociation. The stability of the liquid formulation can be a cold storage conditions stability, a room temperature stability or an elevated temperature stability. The improved stability of the liquid protein formulation can be is manifested by a percent monomer that is higher than the percent monomer in the control formulation, wherein the percent monomer is measured by size exclusion chromatography. The stability of the liquid formulation can be a mechanical stability, which can be manifested by an improved tolerance for a stress condition selected from the group consisting of agitation, pumping, filtering, filling, and gas bubble contact.

Also disclosed herein, in embodiments, are liquid formulations comprising a protein and an excipient compound selected from the group consisting of hindered amine compounds, aromatic compounds, functionalized amino acids, oligopeptides, short-chain organic acids, low molecular weight aliphatic polyacids, and sulfones wherein the presence of the excipient compound in the formulation results in a more stable protein-protein interaction as measured by the protein diffusion interaction parameter kD, or the osmotic virial coefficient B22. In embodiments, the formulation is a therapeutic formulation, and comprises a therapeutic protein. In embodiments, the formulation is a non-therapeutic formulation, and comprises a non-therapeutic protein.

Further disclosed herein, in embodiments, are methods of improving a protein-related process comprising providing the liquid formulation described above, and employing it in a processing method. In embodiments, the processing method includes filtration, pumping, mixing, centrifugation, purification, membrane separation, lyophilization, or chromatography.

DETAILED DESCRIPTION

Figure 1:
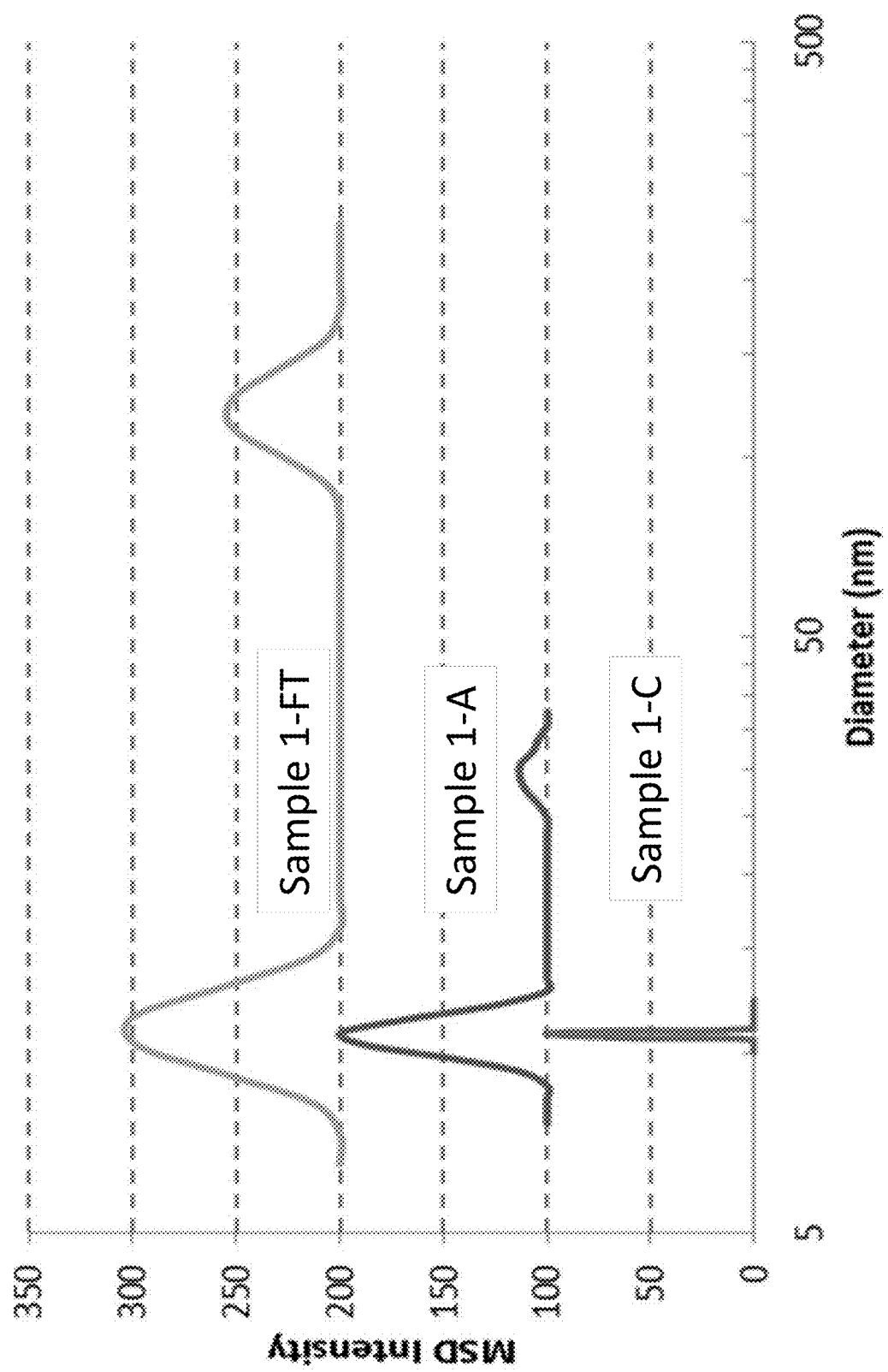
FIG. 1 shows a graph of particle size distributions for solutions of a monoclonal antibody under stressed and non-stressed conditions, as evaluated by Dynamic Light Scattering. The data curves in FIG. 1 have a baseline offset to allow comparison: the curve for Sample 1-A is offset by 100 intensity units and the curve for Sample 1-FT is offset by 200 intensity units in the Y-axis.

Disclosed herein are formulations and methods for their production and use that permit the delivery of concentrated protein solutions. In embodiments, the approaches disclosed herein can yield a lower viscosity liquid formulation or a higher concentration of therapeutic or nontherapeutic proteins in the liquid formulation, as compared to traditional protein solutions. In embodiments, the approaches disclosed herein can yield a liquid formulation having improved stability when compared to a traditional protein solution. A stable formulation is one in which the protein contained therein substantially retains its physical and chemical stability and its therapeutic or nontherapeutic efficacy upon storage under storage conditions, whether cold storage conditions, room temperature conditions, or elevated temperature storage conditions. Advantageously, a stable formulation can also offer protection against aggregation or precipitation of the proteins dissolved therein. For example, the cold storage conditions can entail storage in a refrigerator or freezer. In some examples, cold storage conditions can entail storage at a temperature of 10° C. or less. In additional examples, the cold storage conditions entail storage at a temperature from about 2° to about 10° C. In other examples, the cold storage conditions entail storage at a temperature of about 4° C. In additional examples, the cold storage conditions entail storage at freezing temperature such as about −20° C. or lower. In another example, cold storage conditions entail storage at a temperature of about −20° C. to about 0° C. The room temperature storage conditions can entail storage at ambient temperatures, for example, from about 10° C. to about 30° C. Elevated storage conditions can entail storage at a temperature greater than about 30° C. Elevated temperature stability, for example at temperatures from about 30° C. to about 50° C., can be used as part an accelerated aging study to predict the long term storage at typical ambient (10-30° C.) conditions.

It is well known to those skilled in the art of polymer science and engineering that proteins in solution tend to form entanglements, which can limit the translational mobility of the entangled chains and interfere with the protein's therapeutic or nontherapeutic efficacy. In embodiments, excipient compounds as disclosed herein can suppress protein clustering due to specific interactions between the excipient compound and the target protein in solution. Excipient compounds as disclosed herein can be natural or synthetic.

1. Definitions

For the purpose of this disclosure, the term "protein" refers to a sequence of amino acids having a chain length long enough to produce a discrete tertiary structure, typically having a molecular weight between 1-3000 kDa. In some embodiments, the molecular weight of the protein is between about 50-200 kDa; in other embodiments, the molecular weight of the protein is between about 20-1000 kDa or between about 20-2000 kDa. In contrast to the term "protein," the term "peptide" refers to a sequence of amino acids that does not have a discrete tertiary structure. A wide variety of biopolymers are included within the scope of the term "protein." For example, the term "protein" can refer to therapeutic or non-therapeutic proteins, including antibodies, aptamers, fusion proteins, PEGylated proteins, synthetic polypeptides, protein fragments, lipoproteins, enzymes, structural peptides, and the like.

a. Therapeutic Biopolymers Definitions

Those biopolymers having therapeutic effects may be termed "therapeutic biopolymers." Those proteins having therapeutic effects may be termed "therapeutic proteins." Formulations containing therapeutic proteins in therapeutically effective amounts may be termed "therapeutic formulations." The therapeutic protein contained in a therapeutic formulation may also be termed its "protein active ingredient." In embodiments, a therapeutic formulation comprises a therapeutically effective amount of a protein active ingredient and an excipient, with or without other optional components. As used herein, the term "therapeutic" includes both treatments of existing disorders and preventions of disorders.

A "treatment" includes any measure intended to cure, heal, alleviate, improve, remedy, or otherwise beneficially affect the disorder, including preventing or delaying the onset of symptoms and/or alleviating or ameliorating symptoms of the disorder. Those patients in need of a treatment include both those who already have a specific disorder, and those for whom the prevention of a disorder is desirable. A disorder is any condition that alters the homeostatic well-being of a mammal, including acute or chronic diseases, or pathological conditions that predispose the mammal to an acute or chronic disease. Non-limiting examples of disorders include cancers, metabolic disorders (e.g., diabetes), allergic disorders (e.g., asthma), dermatological disorders, cardiovascular disorders, respiratory disorders, hematological disorders, musculoskeletal disorders, inflammatory or rheumatological disorders, autoimmune disorders, gastrointestinal disorders, urological disorders, sexual and reproductive disorders, neurological disorders, and the like. The term "mammal" for the purposes of treatment can refer to any animal classified as a mammal, including humans, domestic animals, pet animals, farm animals, sporting animals, working animals, and the like. A "treatment" can therefore include both veterinary and human treatments. For convenience, the mammal undergoing such "treatment" can be referred to as a "patient." In certain embodiments, the patient can be of any age, including fetal animals in utero.

In embodiments, a treatment involves providing a therapeutically effective amount of a therapeutic formulation to a mammal in need thereof. A "therapeutically effective amount" is at least the minimum concentration of the therapeutic protein administered to the mammal in need thereof, to effect a treatment of an existing disorder or a prevention of an anticipated disorder (either such treatment or such prevention being a "therapeutic intervention"). Therapeutically effective amounts of various therapeutic proteins that may be included as active ingredients in the therapeutic formulation may be familiar in the art; or, for therapeutic proteins discovered or applied to therapeutic interventions hereinafter, the therapeutically effective amount can be determined by standard techniques carried out by those having ordinary skill in the art, using no more than routine experimentation.

Therapeutic proteins include, for example, proteins such as bevacizumab, trastuzumab, adalimumab, infliximab, etanercept, darbepoetin alfa, epoetin alfa, cetuximab, filgrastim, and rituximab. Other therapeutic proteins will be familiar to those having ordinary skill in the art: as further non-limiting examples, therapeutic proteins can include mammalian proteins such as hormones and prohormones (e.g., insulin and proinsulin, glucagon, calcitonin, thyroid hormones (T3 or T4 or thyroid-stimulating hormone), parathyroid hormone, follicle-stimulating hormone, luteinizing hormone, growth hormone, growth hormone releasing factor, and the like); clotting and anti-clotting factors (e.g., tissue factor, von Willebrand's factor, Factor VIIIC, Factor IX, protein C, plasminogen activators (urokinase, tissue-type plasminogen activators), thrombin); cytokines, chemokines, and inflammatory mediators; interferons; colony-stimulating factors; interleukins (e.g., IL-1 through IL-10); growth factors (e.g., vascular endothelial growth factors, fibroblast growth factor, platelet-derived growth factor, transforming growth factor, neurotrophic growth factors, insulin-like growth factor, and the like); albumins; collagens and elastins; hematopoietic factors (e.g., erythropoietin, thrombopoietin, and the like); osteoinductive factors (e.g., bone morphogenetic protein); receptors (e.g., integrins, cadherins, and the like); surface membrane proteins; transport proteins; regulatory proteins; antigenic proteins (e.g., a viral component that acts as an antigen); and antibodies. The term "antibody" is used herein in its broadest sense, to include as non-limiting examples monoclonal antibodies (including, for example, full-length antibodies with an immunoglobulin Fc region), single-chain molecules, bi-specific and multi-specific antibodies, diabodies, antibody compositions having polyepitopic specificity, and fragments of antibodies (including, for example, Fab, Fv, and F(ab')2). Antibodies can also be termed "immunoglobulins." An antibody is understood to be directed against a specific protein or non-protein "antigen," which is a biologically important material; the administration of a therapeutically effective amount of an antibody to a patient can complex with the antigen, thereby altering its biological properties so that the patient experiences a therapeutic effect.

In embodiments, the proteins are PEGylated, meaning that they comprise poly(ethylene glycol) ("PEG") and/or poly(propylene glycol) ("PPG") units. PEGylated proteins, or PEG-protein conjugates, have found utility in therapeutic applications due to their beneficial properties such as solubility, pharmacokinetics, pharmacodynamics, immunogenicity, renal clearance, and stability. Non-limiting examples of PEGylated proteins are PEGylated versions of cytokines, hormones, hormone receptors, cell signaling factors, clotting factors, antibodies, antibody fragments, peptides, aptamers, and enzymes. In embodiments, the PEGylated proteins can be interferons (PEG-IFN), PEGylated anti-vascular endothelial growth factor (VEGF), PEGylated human growth hormones (HGH), PEGylated mutein antagonists, PEG protein conjugate drugs, Adagen, PEG-adenosine deaminase, PEG-uricase, Pegaspargase, PEGylated granulocyte colony-stimulating factors (GCSF), Pegfilgrastim, Pegloticase, Pegvisomant, Pegaptanib, Peginesatide, PEGylated erythropoiesis-stimulating agents, PEGylated epoetin-α, PEGylated epoetin-β, methoxy polyethylene glycol-epoetin beta, PEGylated antihemophilic factor VIII, PEGylated antihemophilic factor IX, and Certolizumab pegol.

PEGylated proteins can be synthesized by a variety of methods such as a reaction of protein with a PEG reagent having one or more reactive functional groups. The reactive functional groups on the PEG reagent can form a linkage with the protein at targeted protein sites such as lysine, histidine, cysteine, and the N-terminus. Typical PEGylation reagents have reactive functional groups such as aldehyde, maleimide, or succinimide groups that have specific reactivity with targeted amino acid residues on proteins. The PEGylation reagents can have a PEG chain length from about 1 to about 1000 PEG and/or PPG repeating units. Other methods of PEGylation include glyco-PEGylation, where the protein is first glycosylated and then the glycosylated residues are PEGylated in a second step. Certain PEGylation processes are assisted by enzymes like sialyl-transferase and transglutaminase.

While the PEGylated proteins can offer therapeutic advantages over native, non-PEGylated proteins, these materials can have physical or chemical properties that make them difficult to purify, dissolve, filter, concentrate, and administer. The PEGylation of a protein can lead to a higher solution viscosity compared to the native protein, and this generally requires the formulation of PEGylated protein solutions at lower concentrations.

It is desirable to formulate protein therapeutics in stable, low viscosity solutions so they can be administered to patients in a minimal injection volume. For example, the subcutaneous (SC) or intramuscular (IM) injection of drugs generally requires a small injection volume, preferably less than 2 mL. The SC and IM injection routes are well suited to self-administered care, and this is a less costly and more accessible form of treatment compared with intravenous (IV) injection which is only conducted under direct medical supervision. Formulations for SC or IM injection require a low solution viscosity, generally below 30 cP, and preferably below 20 cP, to allow easy flow of the therapeutic solution through a narrow gauge needle with minimal injection force. This combination of small injection volume and low viscosity requirements present a challenge to the use of PEGylated protein therapeutics in SC or IM injection routes.

b. Non-Therapeutic Biopolymers Definitions

Those biopolymers used for non-therapeutic purposes (i.e., purposes not involving treatments), such as household, nutrition, commercial, and industrial applications, may be termed "non-therapeutic biopolymers." Those proteins used for non-therapeutic purposes may be termed "non-therapeutic proteins." Formulations containing non-therapeutic proteins may be termed "non-therapeutic formulations." The non-therapeutic proteins can be derived from plant sources, animal sources, or produced from cell cultures; they also can be enzymes or structural proteins. The non-therapeutic proteins can be used in in household, nutrition, commercial, and industrial applications such as catalysts, human and animal nutrition, processing aids, cleaners, and waste treatment.

An important category of non-therapeutic proteins is the category of enzymes. Enzymes have a number of non-therapeutic applications, for example, as catalysts, human and animal nutritional ingredients, processing aids, cleaners, and waste treatment agents. Enzyme catalysts are used to accelerate a variety of chemical reactions. Examples of enzyme catalysts for non-therapeutic uses include catalases, oxidoreductases, transferases, hydrolases, lyases, isomerases, and ligases. Human and animal nutritional uses of enzymes include nutraceuticals, nutritive sources of protein, chelation or controlled delivery of micronutrients, digestion aids, and supplements; these can be derived from amylase, protease, trypsin, lactase, and the like. Enzymatic processing aids are used to improve the production of food and beverage products in operations like baking, brewing, fermenting, juice processing, and winemaking. Examples of these food and beverage processing aids include amylases, cellulases, pectinases, glucanases, lipases, and lactases. Enzymes can also be used in the production of biofuels. Ethanol for biofuels, for example, can be aided by the enzymatic degradation of biomass feedstocks such as cellulosic and lignocellulosic materials. The treatment of such feedstock materials with cellulases and ligninases transforms the biomass into a substrate that can be fermented into fuels. In other commercial applications, enzymes are used as detergents, cleaners, and stain lifting aids for laundry, dish washing, surface cleaning, and equipment cleaning applications. Typical enzymes for this purpose include proteases, cellulases, amylases, and lipases. In addition, non-therapeutic enzymes are used in a variety of commercial and industrial processes such as textile softening with cellulases, leather processing, waste treatment, contaminated sediment treatment, water treatment, pulp bleaching, and pulp softening and debonding. Typical enzymes for these purposes are amylases, xylanases, cellulases, and ligninases.

Other examples of non-therapeutic biopolymers include fibrous or structural proteins such as keratins, collagen, gelatin, elastin, fibroin, actin, tubulin, or the hydrolyzed, degraded, or derivatized forms thereof. These materials are used in the preparation and formulation of food ingredients such as gelatin, ice cream, yogurt, and confections; they area also added to foods as thickeners, rheology modifiers, mouthfeel improvers, and as a source of nutritional protein. In the cosmetics and personal care industry, collagen, elastin, keratin, and hydrolyzed keratin are widely used as ingredients in skin care and hair care formulations. Still other examples of non-therapeutic biopolymers are whey proteins such as beta-lactoglobulin, alpha-lactalbumin, and serum albumin. These whey proteins are produced in mass scale as a byproduct from dairy operations and have been used for a variety of non-therapeutic applications.

2. Therapeutic Formulations

In one aspect, the formulations and methods disclosed herein provide stable liquid formulations of improved or reduced viscosity, comprising a therapeutic protein in a therapeutically effective amount and an excipient compound. In embodiments, the formulation can improve the stability while providing an acceptable concentration of active ingredients and an acceptable viscosity. In embodiments, the formulation provides an improvement in stability when compared to a control formulation; for the purposes of this disclosure, a control formulation is a formulation containing the protein active ingredient that is substantially similar on a dry weight basis to the therapeutic formulation except that it lacks the excipient compound. In embodiments, the formulation provides an improvement in stability under the stress conditions of long term storage, elevated temperatures such as 25-45° C., freeze/thaw conditions, shear or mixing, syringing, dilution, gas bubble exposure, oxygen exposure, light exposure, and lyophilization. In embodiments, improved stability of the protein-containing formulation is in the form of lower percentage of soluble aggregates, particulates, subvisible particles, or gel formation, compared to a control formulation. In embodiments, improved stability of the protein-containing formulation is in the form of higher biological activity compared to a control formulation. In embodiments, improved stability of the protein-containing formulation is in the form of improved chemical stability, such as resistance to a chemical reaction such as hydrolysis, photolysis, oxidation, reduction, deamidation, disulfide scrambling, fragmentation, or dissociation. In embodiments, improved stability of the protein-containing formulation is manifested by a decrease in the formation of visible particles, subvisible particles, aggregates, turbidity, opalescence, or gel.

It is understood that the viscosity of a liquid protein formulation can be affected by a variety of factors, including but not limited to: the nature of the protein itself (e.g., enzyme, antibody, receptor, fusion protein, etc.); its size, three-dimensional structure, chemical composition, and molecular weight; its concentration in the formulation; the components of the formulation besides the protein; the desired pH range; the storage conditions for the formulation; and the method of administering the formulation to the patient. Therapeutic proteins most suitable for use with the excipient compounds described herein are preferably essentially pure, i.e., free from contaminating proteins. In embodiments, an "essentially pure" therapeutic protein is a protein composition comprising at least 90% by weight of the therapeutic protein, or preferably at least 95% by weight of therapeutic protein, or more preferably, at least 99% by weight of the therapeutic protein, all based on the total weight of therapeutic proteins and contaminating proteins in the composition. For the purposes of clarity, a protein added as an excipient is not intended to be included in this definition. The therapeutic formulations described herein are intended for use as pharmaceutical-grade formulations, i.e., formulations intended for use in treating a mammal, in such a form that the desired therapeutic efficacy of the protein active ingredient can be achieved, and without containing components that are toxic to the mammal to whom the formulation is to be administered.

In embodiments, the therapeutic formulation contains at least 1 mg/mL of protein active ingredient. In other embodiments, the therapeutic formulation contains at least 10 mg/mL of protein active ingredient. In other embodiments, the therapeutic formulation contains at least 50 mg/mL of protein active ingredient. In other embodiments, the therapeutic formulation contains at least 100 mg/mL of protein active ingredient. In yet other embodiments, the therapeutic formulation solution contains at least 200 mg/mL of protein active ingredient. Generally, the excipient compounds disclosed herein are added to the therapeutic formulation in an amount between about 0.001 to about 60 mg/mL. In embodiments, the excipient compound can be added in an amount of about 0.1 to about 50 mg/mL. In embodiments, the excipient compound can be added in an amount of about 1 to about 40 mg/mL. In embodiments, the excipient can be added in an amount of about 5 to about 30 mg/mL.

In certain embodiments, the therapeutic formulation solution contains at least 300 mg/mL of protein active ingredient. In certain aspects, the excipient compounds disclosed herein are added to the therapeutic formulation in an amount between about 1 to about 300 mg/mL. In embodiments, the excipient compound can be added in an amount of about 5 to about 100 mg/mL. In embodiments, the excipient compound can be added in an amount of about 10 to about 75 mg/mL. In embodiments, the excipient can be added in an amount of about 15 to about 50 mg/mL.

Excipient compounds of various molecular weights are selected for specific advantageous properties when combined with the protein active ingredient in a formulation. Examples of therapeutic formulations comprising excipient compounds are provided below. In embodiments, the excipient compound has a molecular weight of <5000 Da. In embodiments, the excipient compound has a molecular weight of <1000 Da. In embodiments, the excipient compound has a molecular weight of <500 Da.

In embodiments, an excipient compound as disclosed herein is added to the therapeutic formulation in a viscosity-reducing amount. In embodiments, a viscosity-reducing amount is the amount of an excipient compound that reduces the viscosity of the formulation at least 10% when compared to a control formulation; for the purposes of this disclosure, a control formulation is a formulation containing the protein active ingredient that is substantially similar on a dry weight basis to the therapeutic formulation except that it lacks the excipient compound. In embodiments, the viscosity-reducing amount is the amount of an excipient compound that reduces the viscosity of the formulation at least 30% when compared to the control formulation. In embodiments, the viscosity-reducing amount is the amount of an excipient compound that reduces the viscosity of the formulation at least 50% when compared to the control formulation. In embodiments, the viscosity-reducing amount is the amount of an excipient compound that reduces the viscosity of the formulation at least 70% when compared to the control formulation. In embodiments, the viscosity-reducing amount is the amount of an excipient compound that reduces the viscosity of the formulation at least 90% when compared to the control formulation.

In embodiments, the viscosity-reducing amount yields a therapeutic formulation having a viscosity of less than 100 cP. In other embodiments, the therapeutic formulation has a viscosity of less than 50 cP. In other embodiments, the therapeutic formulation has a viscosity of less than 20 cP. In yet other embodiments, the therapeutic formulation has a viscosity of less than 10 cP. The term "viscosity" as used herein refers to a dynamic viscosity value when measured by the methods disclosed herein.

In embodiments, the therapeutic formulations are administered to a patient at high concentration of therapeutic protein. In embodiments, the therapeutic formulations are administered to patients in a smaller injection volume and/or with less discomfort than would be experienced with a similar formulation lacking the therapeutic excipient. In embodiments, the therapeutic formulations are administered to patients using a narrower gauge needle, or less syringe force that would be required with a similar formulation lacking the therapeutic excipient. In embodiments, the therapeutic formulations are administered as a depot injection. In embodiments, the therapeutic formulations extend the half-life of the therapeutic protein in the body. These features of therapeutic formulations as disclosed herein would permit the administration of such formulations by intramuscular or subcutaneous injection in a clinical situation, i.e., a situation where patient acceptance of an intramuscular injection would include the use of small-bore needles typical for IM/SC purposes and the use of a tolerable (for example, 2-3 cc) injected volume, and where these conditions result in the administration of an effective amount of the formulation in a single injection at a single injection site. By contrast, injection of a comparable dosage amount of the therapeutic protein using conventional formulation techniques would be limited by the higher viscosity of the conventional formulation, so that a SC/IM injection of the conventional formulation would not be suitable for a clinical situation.

Therapeutic formulations in accordance with this disclosure can have certain advantageous properties consistent with improved stability. In embodiments, the therapeutic formulations are resistant to shear degradation, phase separation, clouding out, precipitation, oxidation, deamidation, aggregation, and/or denaturing. In embodiments, the therapeutic formulations are processed, purified, stored, syringed, dosed, filtered, and/or centrifuged more effectively, compared with a control formulation.

In embodiments, the therapeutic formulations disclosed herein are resistant to monomer loss as measured by size exclusion chromatography (SEC) analysis. In SEC analysis, the main analyte peak is generally associated with the active component of the formulation, such as a therapeutic protein, and this main peak of the active component is referred to as the monomer peak. The monomer peak represents the amount of active component in the monomeric state, as opposed to aggregated (dimeric, trimeric, oligomeric, etc.) or fragmented states. The monomer peak area can be compared with the total area of the monomer, aggregate, and fragment peaks associated with the protein. Thus, the stability of a therapeutic formulation can be observed by the relative amount of monomer after an elapsed time. In embodiments, an ideal stability result is to have from 98 to 100% monomer peak as determined by SEC analysis. In embodiments, an improvement in stability of a therapeutic formulation as disclosed herein can be measured as a higher percent monomer after a certain elapsed time, as compared to the percent monomer in a control formulation that does not contain the excipient. In embodiments, an improvement in stability of a therapeutic formulation as disclosed herein can be measured as a higher percent monomer after exposure to a stress condition, as compared to the percent monomer in a control formulation that does not contain the excipient after exposure to the stress condition. In embodiments, the stress conditions can be a low temperature storage, high temperature storage, exposure to air, exposure to gas bubbles, exposure to shear conditions, or exposure to freeze/thaw cycles.

In embodiments, the therapeutic formulations of the invention are resistant to an increase in protein particle size as measured by dynamic light scattering (DLS) analysis. In DLS analysis, the particle size of the therapeutic protein can be observed as a median particle diameter. Ideally, the median particle diameter of the therapeutic protein should be relatively unchanged since the particle diameter represents the active component in the monomeric state, as opposed to aggregated (dimeric, trimeric, oligomeric, etc.) or fragmented states. An increase of the median particle diameter, therefore, can represent an aggregated protein. Thus, the stability of a therapeutic formulation can be observed by the relative change in median particle diameter after an elapsed time. In embodiments, the therapeutic formulations as disclosed herein are resistant to forming a polydisperse particle size distribution as measured by dynamic light scattering (DLS) analysis. In embodiments, a therapeutic protein formulation can contain a monodisperse particle size distribution of colloidal protein particles. In embodiments, an ideal stability result is to have less than a 10% change in the median particle diameter compared to the initial median particle diameter of the formulation. In embodiments, an improvement in stability of a therapeutic formulation of the invention can be measured as a lower percent change of the median particle diameter after a certain elapsed time, as compared to the median particle diameter in a control formulation that does not contain the excipient. In embodiments, an improvement in stability of a therapeutic formulation as disclosed herein can be measured as a lower percent change of the median particle diameter after exposure to a stress condition, as compared to the percent change of the median particle diameter in a control formulation that does not contain the excipient. In other words, in embodiments, improved stability prevents an increase in particle size as measured by light scattering. In embodiments, the stress conditions can be a low temperature storage, high temperature storage, exposure to air, exposure to gas bubbles, exposure to shear conditions, or exposure to freeze/thaw cycles. In embodiments, an improvement in stability of a therapeutic formulation as disclosed herein can be measured as a less polydisperse particle size distribution as measured by DLS, as compared to the polydispersity of the particle size distribution in a control formulation that does not contain the excipient.

In embodiments, the therapeutic formulations as disclosed herein are resistant to precipitation as measured by turbidity, light scattering, or particle counting analysis. In turbidity, light scattering, or particle counting analysis, a lower value generally represents a lower number of suspended particles in a formulation. An increase of turbidity, light scattering, or particle counting can indicate that the solution of the therapeutic protein is not stable. Thus, the stability of a therapeutic formulation can be observed by the relative amount of turbidity, light scattering, or particle counting after an elapsed time. In embodiments, an ideal stability result is to have a low and relatively constant turbidity, light scattering, or particle counting value. In embodiments, an improvement in stability of a therapeutic formulation as disclosed herein can be measured as a lower turbidity, lower light scattering, or lower particle count after a certain elapsed time, as compared to the turbidity, light scattering, or particle count values in a control formulation that does not contain the excipient. In embodiments, an improvement in stability of a therapeutic formulation as disclosed herein can be measured as a lower turbidity, lower light scattering, or lower particle count after exposure to a stress condition, as compared to the turbidity, light scattering, or particle count in a control formulation that does not contain the excipient. In embodiments, the stress conditions can be a low temperature storage, high temperature storage, exposure to air, exposure to gas bubbles, exposure to shear conditions, or exposure to freeze/thaw cycles.

In embodiments, the therapeutic excipient has antioxidant properties that stabilize the therapeutic protein against oxidative damage. In embodiments, the therapeutic formulation is stored at ambient temperatures, or for extended time at refrigerator conditions without appreciable loss of potency for the therapeutic protein. In embodiments, the therapeutic formulation is dried down for storage until it is needed; then it is reconstituted with an appropriate solvent, e.g., water. Advantageously, the formulations prepared as described herein can be stable over a prolonged period of time, from months to years. When exceptionally long periods of storage are desired, the formulations can be preserved in a freezer (and later reactivated) without fear of protein denaturation. In embodiments, formulations can be prepared for long-term storage that do not require refrigeration.

In embodiments, the excipient compounds disclosed herein are added to the therapeutic formulation in a stability-improving amount. In embodiments, a stability-improving amount is the amount of an excipient compound that reduces the degradation of the formulation at least 10% when compared to a control formulation; for the purposes of this disclosure, a control formulation is a formulation containing the protein active ingredient that is substantially similar on a weight basis to the therapeutic formulation except that it lacks the excipient compound. In embodiments, the stability-improving amount is the amount of an excipient compound that reduces the degradation of the formulation at least 30% when compared to the control formulation. In embodiments, the stability-improving amount is the amount of an excipient compound that reduces the degradation of the formulation at least 50% when compared to the control formulation. In embodiments, the stability-improving amount is the amount of an excipient compound that reduces the degradation of the formulation at least 70% when compared to the control formulation. In embodiments, the stability-improving amount is the amount of an excipient compound that reduces the degradation of the formulation at least 90% when compared to the control formulation.

Methods for preparing therapeutic formulations may be familiar to skilled artisans. The therapeutic formulations of the present invention can be prepared, for example, by adding the excipient compound to the formulation before or after the therapeutic protein is added to the solution. The therapeutic formulation can, for example, be produced by combining the therapeutic protein and the excipient at a first (lower) concentration and then processed by filtration or centrifugation to produce a second (higher) concentration of the therapeutic protein. Therapeutic formulations can be made with one or more of the excipient compounds with chaotropes, kosmotropes, hydrotropes, and salts. Therapeutic formulations can be made with one or more of the excipient compounds using techniques such as encapsulation, dispersion, liposome, vesicle formation, and the like. Methods for preparing therapeutic formulations comprising the excipient compounds disclosed herein can include combinations of the excipient compounds. In embodiments, combinations of excipients can produce benefits in lower viscosity, improved stability, or reduced injection site pain. Other additives may be introduced into the therapeutic formulations during their manufacture, including preservatives, surfactants, sugars, sucrose, trehalose, polysaccharides, arginine, proline, hyaluronidase, stabilizers, buffers, and the like. As used herein, a pharmaceutically acceptable excipient compound is one that is non-toxic and suitable for animal and/or human administration.

3. Non-Therapeutic Formulations

In one aspect, the formulations and methods disclosed herein provide stable liquid formulations of improved or reduced viscosity, comprising a non-therapeutic protein in an effective amount and an excipient compound. In embodiments, the formulation improves the stability while providing an acceptable concentration of active ingredients and an acceptable viscosity. In embodiments, the formulation provides an improvement in stability when compared to a control formulation; for the purposes of this disclosure, a control formulation is a formulation containing the protein active ingredient that is substantially similar on a dry weight basis to the non-therapeutic formulation except that it lacks the excipient compound.

It is understood that the viscosity of a liquid protein formulation can be affected by a variety of factors, including but not limited to: the nature of the protein itself (e.g., enzyme, structural protein, degree of hydrolysis, etc.); its size, three-dimensional structure, chemical composition, and molecular weight; its concentration in the formulation; the components of the formulation besides the protein; the desired pH range; and the storage conditions for the formulation.

In embodiments, the non-therapeutic formulation contains at least 25 mg/mL of protein active ingredient. In other embodiments, the non-therapeutic formulation contains at least 100 mg/mL of protein active ingredient. In other embodiments, the non-therapeutic formulation contains at least 200 mg/mL of protein active ingredient. In yet other embodiments, the non-therapeutic formulation solution contains at least 300 mg/mL of protein active ingredient. Generally, the excipient compounds disclosed herein are added to the non-therapeutic formulation in an amount between about 0.001 to about 60 mg/mL. In embodiments, the excipient compound is added in an amount of about 0.1 to about 50 mg/mL. In embodiments, the excipient compound is added in an amount of about 1 to about 40 mg/mL. In embodiments, the excipient is added in an amount of about 5 to about 30 mg/mL.

In certain aspects, the excipient compounds disclosed herein are added to the non-therapeutic formulation in an amount between about 5 to about 300 mg/mL. In embodiments, the excipient compound is added in an amount of about 10 to about 200 mg/mL. In embodiments, the excipient compound is added in an amount of about 20 to about 100 mg/mL. In embodiments, the excipient is added in an amount of about 25 to about 75 mg/mL.

Excipient compounds of various molecular weights are selected for specific advantageous properties when combined with the protein active ingredient in a formulation. Examples of non-therapeutic formulations comprising excipient compounds are provided below. In embodiments, the excipient compound has a molecular weight of <5000 Da. In embodiments, the excipient compound has a molecular weight of <1000 Da. In embodiments, the excipient compound has a molecular weight of <500 Da.

In embodiments, an excipient compound as disclosed herein is added to the non-therapeutic formulation in a viscosity-reducing amount. In embodiments, a viscosity-reducing amount is the amount of an excipient compound that reduces the viscosity of the formulation at least 10% when compared to a control formulation; for the purposes of this disclosure, a control formulation is a formulation containing the protein active ingredient that is substantially similar on a dry weight basis to the therapeutic formulation except that it lacks the excipient compound. In embodiments, the viscosity-reducing amount is the amount of an excipient compound that reduces the viscosity of the formulation at least 30% when compared to the control formulation. In embodiments, the viscosity-reducing amount is the amount of an excipient compound that reduces the viscosity of the formulation at least 50% when compared to the control formulation. In embodiments, the viscosity-reducing amount is the amount of an excipient compound that reduces the viscosity of the formulation at least 70% when compared to the control formulation. In embodiments, the viscosity-reducing amount is the amount of an excipient compound that reduces the viscosity of the formulation at least 90% when compared to the control formulation.

In embodiments, the viscosity-reducing amount yields a non-therapeutic formulation having a viscosity of less than 100 cP. In other embodiments, the non-therapeutic formulation has a viscosity of less than 50 cP. In other embodiments, the non-therapeutic formulation has a viscosity of less than 20 cP. In yet other embodiments, the non-therapeutic formulation has a viscosity of less than 10 cP. The term "viscosity" as used herein refers to a dynamic viscosity value.

Non-therapeutic formulations in accordance with this disclosure can have certain advantageous properties. In embodiments, the non-therapeutic formulations are resistant to shear degradation, phase separation, clouding out, precipitation, and denaturing. In embodiments, the therapeutic formulations can be processed, purified, stored, pumped, filtered, and centrifuged more effectively, compared with a control formulation.

In embodiments, the non-therapeutic excipient has antioxidant properties that stabilize the non-therapeutic protein against oxidative damage. In embodiments, the non-therapeutic formulation is stored at ambient temperatures, or for extended time at refrigerator conditions without appreciable loss of potency for the non-therapeutic protein. In embodiments, the non-therapeutic formulation is dried down for storage until it is needed; then it can be reconstituted with an appropriate solvent, e.g., water. Advantageously, the formulations prepared as described herein is stable over a prolonged period of time, from months to years. When exceptionally long periods of storage are desired, the formulations are preserved in a freezer (and later reactivated) without fear of protein denaturation. In embodiments, formulations are prepared for long-term storage that do not require refrigeration.

In embodiments, the excipient compounds disclosed herein are added to the non-therapeutic formulation in a stability-improving amount. In embodiments, a stability-improving amount is the amount of an excipient compound that reduces the degradation of the formulation at least 10% when compared to a control formulation; for the purposes of this disclosure, a control formulation is a formulation containing the protein active ingredient that is substantially similar on a dry weight basis to the therapeutic formulation except that it lacks the excipient compound. In embodiments, the stability-improving amount is the amount of an excipient compound that reduces the degradation of the formulation at least 30% when compared to the control formulation. In embodiments, the stability-improving amount is the amount of an excipient compound that reduces the degradation of the formulation at least 50% when compared to the control formulation. In embodiments, the stability-improving amount is the amount of an excipient compound that reduces the degradation of the formulation at least 70% when compared to the control formulation. In embodiments, the stability-improving amount is the amount of an excipient compound that reduces the degradation of the formulation at least 90% when compared to the control formulation.

Methods for preparing non-therapeutic formulations comprising the excipient compounds disclosed herein may be familiar to skilled artisans. For example, the excipient compound can be added to the formulation before or after the non-therapeutic protein is added to the solution. The non-therapeutic formulation can be produced at a first (lower) concentration and then processed by filtration or centrifugation to produce a second (higher) concentration. Non-therapeutic formulations can be made with one or more of the excipient compounds with chaotropes, kosmotropes, hydrotropes, and salts. Non-therapeutic formulations can be made with one or more of the excipient compounds using techniques such as encapsulation, dispersion, liposome, vesicle formation, and the like. Other additives can be introduced into the non-therapeutic formulations during their manufacture, including preservatives, surfactants, stabilizers, and the like.

4. Excipient Compounds

Several excipient compounds are described herein, each suitable for use with one or more therapeutic or non-therapeutic proteins, and each allowing the formulation to be composed so that it contains the protein(s) at a high concentration. Some of the categories of excipient compounds described below are: (1) hindered amines; (2) aromatics; (3) functionalized amino acids; (4) oligopeptides; (5) short-chain organic acids; (6) low-molecular-weight aliphatic polyacids; and (7) diones and sulfones. Without being bound by theory, the excipient compounds described herein are thought to associate with certain fragments, sequences, structures, or sections of a therapeutic protein that otherwise would be involved in inter-particle (i.e., protein-protein) interactions. The association of these excipient compounds with the therapeutic or non-therapeutic protein can mask the inter-protein interactions such that the proteins can be formulated in high concentration without causing excessive solution viscosity. In embodiments, the excipient compound can result in more stable protein-protein interaction; protein-protein interaction can be measured by the protein diffusion parameter kD, or the osmotic second virial coefficient B22, or by other techniques familiar to skilled artisans.

Excipient compounds advantageously can be water-soluble, therefore suitable for use with aqueous vehicles. In embodiments, the excipient compounds have a water solubility of >1 mg/mL. In embodiments, the excipient compounds have a water solubility of >10 mg/mL. In embodiments, the excipient compounds have a water solubility of >100 mg/mL. In embodiments, the excipient compounds have a water solubility of >500 mg/mL.

Advantageously for therapeutic protein formulations, the excipient compounds can be derived from materials that are biologically acceptable and are non-immunogenic, and are thus suitable for pharmaceutical use. In therapeutic embodiments, the excipient compounds can be metabolized in the body to yield biologically compatible and non-immunogenic byproducts.

a. Excipient Compound Category 1: Hindered Amines

High concentration solutions of therapeutic or non-therapeutic proteins can be formulated with hindered amine small molecules as excipient compounds. As used herein, the term "hindered amine" refers to a small molecule containing at least one bulky or sterically hindered group, consistent with the examples below. Hindered amines can be used in the free base form, in the protonated form, or a combination of the two. In protonated forms, the hindered amines can be associated with an anionic counterion such as chloride, hydroxide, bromide, iodide, fluoride, acetate, formate, phosphate, sulfate, or carboxylate. Hindered amine compounds useful as excipient compounds can contain secondary amine, tertiary amine, quaternary ammonium, pyridinium, pyrrolidone, pyrrolidine, piperidine, morpholine, or guanidinium groups, such that the excipient compound has a cationic charge in aqueous solution at neutral pH. The hindered amine compounds also contain at least one bulky or sterically hindered group, such as cyclic aromatic, cycloaliphatic, cyclohexyl, or alkyl groups. In embodiments, the sterically hindered group can itself be an amine group such as a dialkylamine, trialkylamine, guanidinium, pyridinium, or quaternary ammonium group. Without being bound by theory, the hindered amine compounds are thought to associate with aromatic sections of the proteins such as phenylalanine, tryptophan, and tyrosine, by a cation pi interaction. In embodiments, the cationic group of the hindered amine can have an affinity for the electron rich pi structure of the aromatic amino acid residues in the protein, so that they can shield these sections of the protein, thereby decreasing the tendency of such shielded proteins to associate and agglomerate.

In embodiments, the hindered amine excipient compounds has a chemical structure comprising imidazole, imidazoline, or imidazolidine groups, or salts thereof, such as imidazole, 1-methylimidazole, 4-methylimidazole, 1-hexyl-3-methylimidazolium chloride, histamine, 4-methylhistamine, alpha-methylhistamine, betahistine, beta-alanine, 2-methyl-2-imidazoline, 1-butyl-3-methylimidazolium chloride, uric acid, potassium urate, betazole, carnosine, aspartame, saccharin, acesulfame potassium, xanthine, theophylline, theobromine, caffeine, and anserine. In embodiments, the hindered amine excipient compounds is selected from the group consisting of dimethylethanolamine, dimethylaminopropylamine, triethanolamine, dimethylbenzylamine, dimethylcyclohexylamine, diethylcyclohexylamine, dicyclohexylmethylamine, hexamethylene biguanide, poly(hexamethylene biguanide), imidazole, dimethylglycine, agmatine, diazabicyclo[2.2.2]octane, tetramethylethylenediamine, N,N-dimethylethanolamine, ethanolamine phosphate, glucosamine, choline chloride, phosphocholine, niacinamide, isonicotinamide, N,N-diethyl nicotinamide, nicotinic acid sodium salt, tyramine, 3-aminopyridine, 2,4,6-trimethylpyridine, 3-pyridine methanol, nicotinamide adenosine dinucleotide, biotin, morpholine, N-methylpyrrolidone, 2-pyrrolidinone, procaine, lidocaine, dicyandiamide-taurine adduct, 2-pyridylethylamine, dicyandiamide-benzyl amine adduct, dicyandiamide-alkylamine adduct, dicyandiamide-cycloalkylamine adduct, and dicyandiamide-aminomethanephosphonic acid adducts. In embodiments, a hindered amine compound consistent with this disclosure is formulated as a protonated ammonium salt. In embodiments, a hindered amine compound consistent with this disclosure is formulated as a salt with an inorganic anion or organic anion as the counterion. In embodiments, high concentration solutions of therapeutic or non-therapeutic proteins are formulated with a combination of caffeine with a benzoic acid, a hydroxybenzoic acid, or a benzenesulfonic acid as excipient compounds. In embodiments, the hindered amine excipient compounds are metabolized in the body to yield biologically compatible byproducts. In some embodiments, the hindered amine excipient compound is present in the formulation at a concentration of about 250 mg/ml or less. In additional embodiments, the hindered amine excipient compound is present in the formulation at a concentration of about 10 mg/ml to about 200 mg/ml. In yet additional aspects, the hindered amine excipient compound is present in the formulation at a concentration of about 20 to about 120 mg/ml.

In embodiments, viscosity-reducing excipients in this hindered amine category may include methylxanthines such as caffeine and theophylline, although their use has typically been limited due to their low water solubility. In some applications it may be advantageous to have higher concentrated solutions of these viscosity-reducing excipients despite their low water solubility. For example, in processing it may be advantageous to have a concentrated excipient solution that can be added to a concentrated protein solution so that adding the excipient does not dilute the protein below the desired final concentration. In other cases, despite its low water solubility, additional viscosity-reducing excipient may be necessary to achieve the desired viscosity reduction, stability, tonicity etc. of a final protein formulation. In embodiments, a highly concentrated excipient solution may be formulated (i) as a viscosity-reducing excipient at a concentration 1.5 to 50 times higher than the effective viscosity-reducing amount, or (ii) as a viscosity-reducing excipient at a concentration 1.5 to 50 times higher than its literature reported solubility in pure water at 298 K (e.g., as reported in The Merck Index; Royal Society of Chemistry; Fifteenth Edition, (Apr. 30, 2013)), or both.

Certain co-solutes have been found to substantially increase the solubility limit of these low solubility viscosity-reducing excipients, allowing for excipient solutions at concentrations multiple times higher than literature reported solubility values. These co-solutes can be classified under the general category of hydrotropes. Co-solutes found to provide the greatest improvement in solubility for this application were generally highly soluble in water (>0.25 M) at ambient temperature and physiological pH, and contained either a pyridine or benzene ring. Examples of compounds that may be useful as co-solutes include aniline HCl, isoniacinamide, niacinamide, n-methyltyramine HCl, phenol, procaine HCl, resorcinol, saccharin calcium salt, saccharin sodium salt, sodium aminobenzoic acid, sodium benzoate, sodium parahydroxybenzoate, sodium metahydroxybenzoate, sodium 2,5-dihydroxybenzoate, sodium salicylate, sodium sulfanilate, sodium parahydroxybenzene sulfonate, synephrine, and tyramine HCl.

In embodiments, certain hindered amine excipient compounds can possess other pharmacological properties. As examples, xanthines are a category of hindered amines having independent pharmacological properties, including stimulant properties and bronchodilator properties when systemically absorbed. Representative xanthines include caffeine, aminophylline, 3-isobutyl-1-methylxanthine, paraxanthine, pentoxifylline, theobromine, theophylline, and the like. Methylated xanthines are understood to affect force of cardiac contraction, heart rate, and bronchodilation. In some embodiments, the xanthine excipient compound is present in the formulation at a concentration of about 30 mg/ml or less.

Another category of hindered amines having independent pharmacological properties are the local injectable anesthetic compounds. Local injectable anesthetic compounds are hindered amines that have a three-component molecular structure of (a) a lipophilic aromatic ring, (b) an intermediate ester or amide linkage, and (c) a secondary or tertiary amine. This category of hindered amines is understood to interrupt neural conduction by inhibiting the influx of sodium ions, thereby inducing local anesthesia. The lipophilic aromatic ring for a local anesthetic compound may be formed of carbon atoms (e.g., a benzene ring) or it may comprise heteroatoms (e.g., a thiophene ring). Representative local injectable anesthetic compounds include, but are not limited to, amylocaine, articaine, bupivicaine, butacaine, butanilicaine, chlorprocaine, cocaine, cyclomethycaine, dimethocaine, editocaine, hexylcaine, isobucaine, levobupivacaine, lidocaine, metabutethamine, metabutoxycaine, mepivacaine, meprylcaine, propoxycaine, prilocaine, procaine, piperocaine, tetracaine, trimecaine, and the like. The local injectable anesthetic compounds can have multiple benefits in protein therapeutic formulations, such as reduced viscosity, improved stability, and reduced pain upon injection. In some embodiments, the local anesthetic compound is present in the formulation in a concentration of about 50 mg/ml or less.

In embodiments, a hindered amine having independent pharmacological properties is used as an excipient compound in accordance with the formulations and methods described herein. In some embodiments, the excipient compounds possessing independent pharmacological properties are present in an amount that does not have a pharmacological effect and/or that is not therapeutically effective. In other embodiments, the excipient compounds possessing independent pharmacological properties are present in an amount that does have a pharmacological effect and/or that is therapeutically effective. In certain embodiments, a hindered amine having independent pharmacological properties is used in combination with another excipient compound that has been selected to decrease formulation viscosity, where the hindered amine having independent pharmacological properties is used to impart the benefits of its pharmacological activity. For example, a local injectable anesthetic compound can be used to decrease formulation viscosity and also to reduce pain upon injection of the formulation. The reduction of injection pain can be caused by anesthetic properties; also a lower injection force can be required when the viscosity is reduced by the excipients. Alternatively, a local injectable anesthetic compound can be used to impart the desirable pharmacological benefit of decreased local sensation during formulation injection, while being combined with another excipient compound that reduces the viscosity of the formulation.

b. Excipient Compound Category 2: Aromatics

High concentration solutions of therapeutic or non-therapeutic proteins can be formulated with aromatic small molecule compounds as excipient compounds. The aromatic excipient compounds can contain an aromatic functional group such as phenyl, benzyl, aryl, alkylbenzyl, hydroxybenzyl, phenolic, hydroxyaryl, heteroaromatic group, or a fused aromatic group. The aromatic excipient compounds also can contain a functional group such as carboxylate, oxide, phenoxide, sulfonate, sulfate, phosphonate, phosphate, or sulfide. Aromatic excipients can be anionic, cationic, or uncharged.

A charged aromatic excipient can be described as an acid, a base, or a salt (as applicable), and it can exist in a variety of salt forms. Without being bound by theory, a charged aromatic excipient compound is thought to be a bulky, sterically hindered molecule that can associate with oppositely charged segments of a protein, so that they can shield these sections of the protein, thereby decreasing the interactions between protein molecules that render the protein-containing formulation viscous.

In embodiments, examples of aromatic excipient compounds include anionic aromatic compounds such as salicylic acid, aminosalicylic acid, hydroxybenzoic acid, aminobenzoic acid, para-aminobenzoic acid, benzenesulfonic acid, hydroxybenzenesulfonic acid, naphthalenesulfonic acid, naphthalenedisulfonic acid, hydroquinone sulfonic acid, sulfanilic acid, vanillic acid, vanillin, vanillin-taurine adduct, aminophenol, anthranilic acid, cinnamic acid, coumaric acid, adenosine monophosphate, indole acetic acid, potassium urate, furan dicarboxylic acid, furan-2-acrylic acid, 2-furanpropionic acid, sodium phenylpyruvate, sodium hydroxyphenylpyruvate, dihydroxybenzoic acid, trihydroxybenzoic acid, pyrogallol, benzoic acid, and the salts of the foregoing acids. In embodiments, the anionic aromatic excipient compounds are formulated in the ionized salt form. In embodiments, an anionic aromatic compound is formulated as the salt of a hindered amine, such as dimethylcyclohexylammonium hydroxybenzoate. In embodiments, the anionic aromatic excipient compounds are formulated with various counterions such as organic cations. In embodiments, high concentration solutions of therapeutic or non-therapeutic proteins are formulated with anionic aromatic excipient compounds and caffeine. In embodiments, the anionic aromatic excipient compound is metabolized in the body to yield biologically compatible byproducts.

In embodiments, examples of aromatic excipient compounds include phenols and polyphenols. As used herein, the term "phenol" refers an organic molecule that consists of at least one aromatic group or fused aromatic group bonded to at least one hydroxyl group and the term "polyphenol" refers to an organic molecule that consists of more than one phenol group. Such excipients can be advantageous under certain circumstances, for example when used in formulations with high concentration solutions of therapeutic or nontherapeutic PEGylated proteins to lower solution viscosity. Non-limiting examples of phenols include the benzenediols resorcinol (1,3-benzenediol), catechol (1,2-benzenediol) and hydroquinone (1,4-benzenediol), the benzenetriols hydroxyquinol (1,2,4-benzenetriol), pyrogallol (1,2,3-benzenetriol), and phloroglucinol (1,3,5-benzenetriol), the benzenetetrols 1,2,3,4-Benzenetetrol and 1,2,3,5-Benzenetetrol, and benzenepentol and benzenehexol. Non-limiting examples of polyphenols include tannic acid, ellagic acid, epigallocatechin gallate, catechin, tannins, ellagitannins, and gallotannins. More generally, phenolic and polyphenolic compounds include, but are not limited to, flavonoids, lignans, phenolic acids, and stilbenes. Flavonoid compounds include, but are not limited to, anthocyanins, chalcones, dihydrochalcones, dihydroflavanols, flavanols, flavanones, flavones, flavonols, and isoflavonoids. Phenolic acids include, but are not limited to, hydroxybenzoic acids, hydroxycinnamic acids, hydroxyphenylacetic acids, hydroxyphenylpropanoic acids, and hydroxyphenylpentanoic acids. Other polyphenolic compounds include, but are not limited to, alkylmethoxyphenols, alkylphenols, curcuminoids, hydroxybenzaldehydes, hydroxybenzoketones, hydroxycinnamaldehydes, hydroxycoumarins, hydroxyphenylpropenes, methoxyphenols, naphtoquinones, hydroquinones, phenolic terpenes, resveratrol, and tyrosols. In embodiments, the polyphenol is tannic acid. In embodiments, the phenol is gallic acid. In embodiments, the phenol is pyrogallol. In embodiments, the phenol is resorcinol. Without being bound by theory, the hydroxyl groups of phenolic compounds, e.g., gallic acid, pyrogallol, and resorcinol, form hydrogen bonds with ether oxygen atoms in the backbone of the PEG chain and thus form a phenol/PEG complex that fundamentally alters the PEG solution structure such that the solution viscosity is reduced. Polyphenolic compounds, such as tannic acid, derive their viscosity-reducing properties from their respective phenol group building blocks, such as gallic acid, pyrogallol, and resorcinol. The specific organization of the phenol groups within a polyphenolic compound can give rise to complex behavior in which a viscosity reduction attained by the addition of a phenol is enhanced by the addition of a lower quantity of the respective polyphenol.

c. Excipient Compound Category 3: Functionalized Amino Acids

High concentration solutions of therapeutic or non-therapeutic proteins can be formulated with one or more functionalized amino acids, where a single functionalized amino acid or an oligopeptide comprising one or more functionalized amino acids may be used as the excipient compound. In embodiments, the functionalized amino acid compounds comprise molecules ("amino acid precursors") that can be hydrolyzed or metabolized to yield amino acids. In embodiments, the functionalized amino acids can contain an aromatic functional group such as phenyl, benzyl, aryl, alkylbenzyl, hydroxybenzyl, hydroxyaryl, heteroaromatic group, or a fused aromatic group. In embodiments, the functionalized amino acid compounds can contain esterified amino acids, such as methyl, ethyl, propyl, butyl, benzyl, cycloalkyl, glyceryl, hydroxyethyl, hydroxypropyl, PEG, and PPG esters. In embodiments, the functionalized amino acid compounds are selected from the group consisting of arginine ethyl ester, arginine methyl ester, arginine hydroxyethyl ester, and arginine hydroxypropyl ester. In embodiments, the functionalized amino acid compound is a charged ionic compound in aqueous solution at neutral pH. For example, a single amino acid can be derivatized by forming an ester, like an acetate or a benzoate, and the hydrolysis products would be acetic acid or benzoic acid, both natural materials, plus the amino acid. In embodiments, the functionalized amino acid excipient compounds are metabolized in the body to yield biologically compatible byproducts.

d. Excipient Compound Category 4: Oligopeptides

High concentration solutions of therapeutic or non-therapeutic proteins can be formulated with oligopeptides as excipient compounds. In embodiments, the oligopeptide is designed such that the structure has a charged section and a bulky section. In embodiments, the oligopeptides consist of between 2 and 10 peptide subunits. The oligopeptide can be bi-functional, for example a cationic amino acid coupled to a non-polar one, or an anionic one coupled to a non-polar one. In embodiments, the oligopeptides consist of between 2 and 5 peptide subunits. In embodiments, the oligopeptides are homopeptides such as polyglutamic acid, polyaspartic acid, poly-lysine, poly-arginine, and poly-histidine. In embodiments, the oligopeptides have a net cationic charge. In other embodiments, the oligopeptides are heteropeptides, such as Trp2Lys3. In embodiments, the oligopeptide can have an alternating structure such as an ABA repeating pattern. In embodiments, the oligopeptide can contain both anionic and cationic amino acids, for example, Arg-Glu. Without being bound by theory, the oligopeptides comprise structures that can associate with proteins in such a way that it reduces the intermolecular interactions that lead to high viscosity solutions; for example, the oligopeptide-protein association can be a charge-charge interaction, leaving a somewhat non-polar amino acid to disrupt hydrogen bonding of the hydration layer around the protein, thus lowering viscosity. In some embodiments, the oligopeptide excipient is present in the composition in a concentration of about 50 mg/ml or less.

e. Excipient Compound Category 5: Short-Chain Organic Acids

As used herein, the term "short-chain organic acids" refers to C2-C6 organic acid compounds and the salts, esters, or lactones thereof. This category includes saturated and unsaturated carboxylic acids, hydroxy functionalized carboxylic acids, and linear, branched, or cyclic carboxylic acids. In embodiments, the acid group in the short-chain organic acid is a carboxylic acid, sulfonic acid, phosphonic acid, or a salt thereof.

In addition to the four excipient categories above, high concentration solutions of therapeutic or non-therapeutic proteins can be formulated with short-chain organic acids, for example, the acid or salt forms of sorbic acid, valeric acid, propionic acid, caproic acid, and ascorbic acid as excipient compounds. Examples of excipient compounds in this category include potassium sorbate, taurine, calcium propionate, magnesium propionate, and sodium ascorbate.

f. Excipient Compound Category 6: Low Molecular Weight Aliphatic Polyacids

High concentration solutions of therapeutic or non-therapeutic PEGylated proteins can be formulated with certain excipient compounds that enable lower solution viscosity, where such excipient compounds are low molecular weight aliphatic polyacids. As used herein, the term "low molecular weight aliphatic polyacids" refers to organic aliphatic polyacids having a molecular weight <about 1500, and having at least two acidic groups, where an acidic group is understood to be a proton-donating moiety. Non-limiting examples of acidic groups include carboxylate, phosphonate, phosphate, sulfonate, sulfate, nitrate, and nitrite groups. Acidic groups on the low molecular weight aliphatic polyacid can be in the anionic salt form such as carboxylate, phosphonate, phosphate, sulfonate, sulfate, nitrate, and nitrite; their counterions can be sodium, potassium, lithium, and ammonium. Specific examples of low molecular weight aliphatic polyacids useful for interacting with PEGylated proteins as described herein include maleic acid, tartaric acid, glutaric acid, malonic acid, citric acid, ethylenediaminetetraacetic acid (EDTA), aspartic acid, glutamic acid, alendronic acid, etidronic acid and salts thereof. Further examples of low molecular weight aliphatic polyacids in their anionic salt form include phosphate ($PO_4^{3-}$), hydrogen phosphate ($HPO_4^{3-}$), dihydrogen phosphate ($H_2PO_4^-$), sulfate ($SO_4^{2-}$), bisulfate ($HSO_4^-$), pyrophosphate ($P_2O_7^{4-}$), carbonate ($CO_3^{2}$), and bicarbonate ($HCO_3^-$). The counterion for the anionic salts can be Na, Li, K, or ammonium ion. These excipients can also be used in combination with excipients. As used herein, the low molecular weight aliphatic polyacid can also be an alpha hydroxy acid, where there is a hydroxyl group adjacent to a first acidic group, for example glycolic acid, lactic acid, and gluconic acid and salts thereof. In embodiments, the low molecular weight aliphatic polyacid is an oligomeric form that bears more than two acidic groups, for example polyacrylic acid, polyphosphates, polypeptides and salts thereof. In some embodiments, the low molecular weight aliphatic polyacid excipient is present in the composition in a concentration of about 50 mg/ml or less.

g. Excipient Compound Category 7: Diones and Sulfones

An effective viscosity-reducing excipient can be a molecule containing a sulfone, sulfonamide, or dione functional group that is soluble in pure water to at least 1 g/L at 298K and having a net neutral charge at pH 7. Preferably, the molecule has a molecular weight of less than 1000 g/mol and more preferably less than 500 g/mol. The diones and sulfones effective in reducing viscosity have multiple double bonds, are water soluble, have no net charge at pH 7, and are not strong hydrogen bonding donors. Not to be bound by theory, the double bond character can allow for weak pi-stacking interactions with protein. In embodiments, at high protein concentrations and in proteins that only develop high viscosity at high concentration, charged excipients are not effective because electrostatic interaction is a longer range interaction. Solvated protein surfaces are predominantly hydrophilic, making them water soluble. The hydrophobic regions of proteins are generally shielded within the 3-dimensional structure, but the structure is constantly evolving, unfolding, and re-folding (sometimes called "breathing") and the hydrophobic regions of adjacent proteins can come into contact with each other, leading to aggregation by hydrophobic interactions. The pi-stacking feature of dione and sulfone excipients can mask hydrophobic patches that may be exposed during such "breathing." Another other important role of the excipient can be to disrupt hydrophobic interactions and hydrogen bonding between proteins in close proximity, which will effectively reduce solution viscosity. Dione and sulfone compounds that fit this description include dimethylsulfone, ethyl methyl sulfone, ethyl methyl sulfonyl acetate, ethyl isopropyl sulfone, bis(methylsulfonyl)methane, methane sulfonamide, methionine sulfone, 1,2-cyclopentanedione, 1,3-cyclopentanedione, 1,4-cyclopentanedione, and butane-2,3-dione.

5. Protein/Excipient Solutions: Properties and Processes

In certain embodiments, solutions of therapeutic or non-therapeutic proteins are formulated with the above-identified excipient compounds, such as hindered amines, aromatics, functionalized amino acids, oligopeptides, short-chain organic acids, low molecular weight aliphatic polyacids, and diones and sulfones, to result in improved protein-protein interaction characteristics as measured by the protein diffusion interaction parameter, kD, or the second virial coefficient, B22. As used herein, an "improvement" in protein-protein interaction characteristics achieved by formulations using the above-identified excipient compounds means a decrease in protein-protein interactions. These measurements of kD and B22 can be made using standard techniques in the industry, and can be an indicator of improved solution properties or stability of the protein in solution. For example, a highly negative kD value can indicate that the protein has a strong attractive interaction and this can lead to aggregation, instability, and rheology problems. When formulated in the presence of certain of the above identified excipient compounds, the same protein can have a less negative kD value, or a kD value near or above zero.

In embodiments, certain of the above-described excipient compounds, such as hindered amines, aromatics, functionalized amino acids, oligopeptides, short-chain organic acids, low molecular weight aliphatic polyacids, and/or diones and sulfones are used to improve a protein-related process, such as the manufacture, processing, sterile filling, purification, and analysis of protein-containing solutions, using processing methods such as filtration, syringing, transferring, pumping, mixing, heating or cooling by heat transfer, gas transfer, centrifugation, chromatography, membrane separation, centrifugal concentration, tangential flow filtration, radial flow filtration, axial flow filtration, lyophilization, and gel electrophoresis. These processes and processing methods can have improved efficiency due to the lower viscosity, improved solubility, or improved stability of the proteins in the solution during manufacture, processing, purification, and analysis steps. Additionally, equipment-related processes such as the cleanup, sterilization, and maintenance of protein processing equipment can be facilitated by the use of the above-identified excipients due to decreased fouling, decreased denaturing, lower viscosity, and improved solubility of the protein.

High concentration solutions of therapeutic proteins formulated with the above described excipient compounds can be administered to patients using pre-filled syringes.

EXAMPLES

Materials:
Bovine gamma globulin (BGG), >99% purity, Sigma Aldrich
Histidine, Sigma Aldrich Other materials described in the examples below were from Sigma Aldrich unless otherwise specified.

Example 1: Preparation of Formulations Containing Excipient Compounds and Test Protein Formulations were prepared using an excipient compound and a test protein, where the test protein was intended to simulate either a therapeutic protein that would be used in a therapeutic formulation, or a non-therapeutic protein that would be used in a non-therapeutic formulation. Such formulations were prepared in 50 mM histidine hydrochloride with different excipient compounds for viscosity measurement in the following way. Histidine hydrochloride was first prepared by dissolving 1.94 g histidine (Sigma-Aldrich, St. Louis, MO) in distilled water and adjusting the pH to about 6.0 with 1 M hydrochloric acid (Sigma-Aldrich, St. Louis, MO) and then diluting to a final volume of 250 mL with distilled water in a volumetric flask. Excipient compounds were then dissolved in 50 mM histidine HCl. Lists of excipients are provided below in Examples 4, 5, 6, and 7. In some cases excipient compounds were adjusted to pH 6 prior to dissolving in 50 mM histidine HCl. In this case the excipient compounds were first dissolved in deionized water at about 5 wt % and the pH was adjusted to about 6.0 with either hydrochloric acid or sodium hydroxide. The prepared salt solution was then placed in a convection laboratory oven at about 150 degrees Fahrenheit (about 65 degrees C.) to evaporate the water and isolate the solid excipient. Once excipient solutions in 50 mM histidine HCl had been prepared, the test protein (bovine gamma globulin ("BGG") (Sigma-Aldrich, St. Louis, MO)) was dissolved at a ratio of about 0.336 g BGG per 1 mL excipient solution. This resulted in a final protein concentration of about 280 mg/mL. Solutions of BGG in 50 mM histidine HCl with excipient were formulated in 20 mL vials and allowed to shake at 100 rpm on an orbital shaker table overnight. The solutions were then transferred to 2 mL microcentrifuge tubes and centrifuged for ten minutes at 2300 rpm in an IEC MicroMax microcentrifuge to remove entrained air prior to viscosity measurement.

Example 2: Viscosity Measurement

Viscosity measurements of formulations prepared as described in Example 1 were made with a DV-IIT LV cone and plate viscometer (Brookfield Engineering, Middleboro, MA). The viscometer was equipped with a CP-40 cone and was operated at 3 rpm and 25 degrees C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty-second measurement collection period. The three data points collected were then averaged and recorded as the viscosity for the sample.

Example 3: Protein Concentration Measurement

The concentration of the protein in the experimental solutions was determined by measuring the absorbance of the protein solution at a wavelength of 280 nm in a UV/VIS Spectrometer (Perkin Elmer Lambda 35). First the instrument was calibrated to zero absorbance with a 50 mM histidine buffer at pH 6. Next the protein solutions were diluted by a factor of 300 with the same histidine buffer and the absorbance at 280 nm recorded. The final concentration of the protein in the solution was calculated by using the extinction coefficient value of 1.264 mL/(mg×cm).

Example 4: Formulations with Hindered Amine Excipient Compounds

Formulations containing 280 mg/mL BGG were prepared as described in Example 1, with some samples containing added excipient compounds. In these tests, the hydrochloride salts of dimethylcyclohexylamine (DMCHA), dicyclohexylmethylamine (DCHMA), dimethylaminopropylamine (DMAPA), triethanolamine (TEA), dimethylethanolamine (DMEA), and niacinamide were tested as examples of the hindered amine excipient compounds. Also a hydroxybenzoic acid salt of DMCHA and a taurine-dicyandiamide adduct were tested as examples of the hindered amine excipient compounds. The viscosity of each protein solution was measured as described in Example 2, and the results are presented in Table 1 below, showing the benefit of the added excipient compounds in reducing viscosity.

TABLE 1

| Test Number | Excipient Added | Excipient Concentration (mg/mL) | Viscosity (cP) | Viscosity Reduction |
|---|---|---|---|---|
| 4.1 | None | 0 | 79 | 0% |
| 4.2 | DMCHA-HCl | 28 | 50 | 37% |
| 4.3 | DMCHA-HCl | 41 | 43 | 46% |
| 4.4 | DMCHA-HCl | 50 | 45 | 43% |
| 4.5 | DMCHA-HCl | 82 | 36 | 54% |
| 4.6 | DMCHA-HCl | 123 | 35 | 56% |
| 4.7 | DMCHA-HCl | 164 | 40 | 49% |
| 4.8 | DMAPA-HCl | 87 | 57 | 28% |
| 4.9 | DMAPA-HCl | 40 | 54 | 32% |
| 4.10 | DCHMA-HCl | 29 | 51 | 35% |
| 4.11 | DCHMA-HCl | 50 | 51 | 35% |
| 4.14 | TEA-HCl | 97 | 51 | 35% |
| 4.15 | TEA-HCl | 38 | 57 | 28% |
| 4.16 | DMEA-HCl | 51 | 51 | 35% |
| 4.17 | DMEA-HCl | 98 | 47 | 41% |
| 4.20 | DMCHA-hydroxybenzoate | 67 | 46 | 42% |
| 4.21 | DMCHA-hydroxybenzoate | 92 | 42 | 47% |
| 4.22 | Product of Example 8 | 26 | 58 | 27% |
| 4.23 | Product of Example 8 | 58 | 50 | 37% |
| 4.24 | Product of Example 8 | 76 | 49 | 38% |
| 4.25 | Product of Example 8 | 103 | 46 | 42% |
| 4.26 | Product of Example 8 | 129 | 47 | 41% |
| 4.27 | Product of Example 8 | 159 | 42 | 47% |
| 4.28 | Product of Example 8 | 163 | 42 | 47% |
| 4.29 | Niacinamide | 48 | 39 | 51% |
| 4.30 | N-Methyl-2-pyrrolidone | 30 | 45 | 43% |
| 4.31 | N-Methyl-2-pyrrolidone | 52 | 52 | 34% |

Example 5: Formulations with Anionic Aromatic Excipient Compounds

Formulations of 280 mg/mL BGG were prepared as described in Example 1, with some samples containing added excipient compounds. The viscosity of each solution was measured as described in Example 2, and the results are presented in Table 2 below, showing the benefit of the added excipient compounds in reducing viscosity.

TABLE 2

| Test Number | Excipient Added | Excipient Concentration (mg/mL) | Viscosity (cP) | Viscosity Reduction |
|---|---|---|---|---|
| 5.1 | None | 0 | 79 | 0% |
| 5.2 | Sodium aminobenzoate | 43 | 48 | 39% |
| 5.3 | Sodium hydroxybenzoate | 26 | 50 | 37% |
| 5.4 | Sodium sulfanilate | 44 | 49 | 38% |
| 5.5 | Sodium sulfanilate | 96 | 42 | 47% |
| 5.6 | Sodium indole acetate | 52 | 58 | 27% |
| 5.7 | Sodium indole acetate | 27 | 78 | 1% |
| 5.8 | Vanillic acid, sodium salt | 25 | 56 | 29% |
| 5.9 | Vanillic acid, sodium salt | 50 | 50 | 37% |
| 5.10 | Sodium salicylate | 25 | 57 | 28% |
| 5.11 | Sodium salicylate | 50 | 52 | 34% |
| 5.12 | Adenosine monophosphate | 26 | 47 | 41% |
| 5.13 | Adenosine monophosphate | 50 | 66 | 16% |
| 5.14 | Sodium benzoate | 31 | 61 | 23% |
| 5.15 | Sodium benzoate | 56 | 62 | 22% |

Example 6: Formulations with Oligopeptide Excipient Compounds

Oligopeptides (n=5) were synthesized by NeoBioLab Inc. (Woburn, MA) in >9500 purity with the N terminus as a free amine and the C terminus as a free acid. Dipeptides (n=2) were synthesized by LifeTein LLC in 95% purity. Formulations of 280 mg/mL BGG were prepared as described in Example 1, with some samples containing the synthetic oligopeptides as added excipient compounds. The viscosity of each solution was measured as described in Example 2, and the results are presented in Table 3 below, showing the benefit of the added excipient compounds in reducing viscosity.

TABLE 3

| Test Number | Excipient Added | Excipient Concentration (mg/mL) | Viscosity (cP) | Viscosity Reduction |
|---|---|---|---|---|
| 6.1 | None | 0 | 79 | 0% |
| 6.2 | ArgX5 | 100 | 55 | 30% |
| 6.3 | ArgX5 | 50 | 54 | 32% |
| 6.4 | HisX5 | 100 | 62 | 22% |
| 6.5 | HisX5 | 50 | 51 | 35% |
| 6.6 | HisX5 | 25 | 60 | 24% |
| 6.7 | Trp2Lys3 | 100 | 59 | 25% |
| 6.8 | Trp2Lys3 | 50 | 60 | 24% |
| 6.9 | AspX5 | 100 | 102 | −29% |
| 6.10 | AspX5 | 50 | 82 | −4% |
| 6.11 | Dipeptide LE (Leu-Glu) | 50 | 72 | 9% |
| 6.12 | Dipeptide YE (Tyr-Glu) | 50 | 55 | 30% |
| 6.13 | Dipeptide RP (Arg-Pro) | 50 | 51 | 35% |
| 6.14 | Dipeptide RK (Arg-Lys) | 50 | 53 | 33% |
| 6.15 | Dipeptide RH (Arg-His) | 50 | 52 | 34% |
| 6.16 | Dipeptide RR (Arg-Arg) | 50 | 57 | 28% |
| 6.17 | Dipeptide RE (Arg-Glu) | 50 | 50 | 37% |
| 6.18 | Dipeptide LE (Leu-Glu) | 100 | 87 | −10% |
| 6.19 | Dipeptide YE (Tyr-Glu) | 100 | 68 | 14% |
| 6.20 | Dipeptide RP (Arg-Pro) | 100 | 53 | 33% |
| 6.21 | Dipeptide RK (Arg-Lys) | 100 | 64 | 19% |
| 6.22 | Dipeptide RH (Arg-His) | 100 | 72 | 9% |
| 6.23 | Dipeptide RR (Arg-Arg) | 100 | 62 | 22% |
| 6.24 | Dipeptide RE (Arg-Glu) | 100 | 66 | 16% |

Example 8: Synthesis of Guanyl Taurine Excipient

Guanyl taurine was prepared following method described in U.S. Pat. No. 2,230,965. Taurine (Sigma-Aldrich, St. Louis, MO) 3.53 parts were mixed with 1.42 parts of dicyandiamide (Sigma-Aldrich, St. Louis, MO) and grinded in a mortar and pestle until a homogeneous mixture was obtained. Next the mixture was placed in a flask and heated at 200° C. for 4 hours. The product was used without further purification.

Example 9: Protein Formulations Containing Excipient Compounds

Formulations were prepared using an excipient compound and a test protein, where the test protein was intended to simulate either a therapeutic protein that would be used in a therapeutic formulation, or a non-therapeutic protein that would be used in a non-therapeutic formulation. Such formulations were prepared in 50 mM aqueous histidine hydrochloride buffer solution with different excipient compounds for viscosity measurement in the following way. Histidine hydrochloride buffer solution was first prepared by dissolving 1.94 g histidine (Sigma-Aldrich, St. Louis, MO) in distilled water and adjusting the pH to about 6.0 with 1 M hydrochloric acid (Sigma-Aldrich, St. Louis, MO) and then diluting to a final volume of 250 mL with distilled water in a volumetric flask. Excipient compounds were then dissolved in the 50 mM histidine HCl buffer solution. A list of the excipient compounds is provided in Table 4. In some cases, excipient compounds were dissolved in 50 mM histidine HCl and the resulting solution pH was adjusted with small amounts of concentrated sodium hydroxide or hydrochloric acid to achieve pH 6 prior to dissolution of the model protein. In some cases, excipient compounds were adjusted to pH 6 prior to dissolving in 50 mM histidine HCl. In this case the excipient compounds were first dissolved in deionized water at about 5 wt % and the pH was adjusted to about 6.0 with either hydrochloric acid or sodium hydroxide. The prepared salt solution was then placed in a convection laboratory oven at about 150 degrees Fahrenheit (65 degrees C.) to evaporate the water and isolate the solid excipient. Once excipient solutions in 50 mM histidine HCl had been prepared, the test protein, bovine gamma globulin (Sigma-Aldrich, St. Louis, MO) was dissolved at a ratio to achieve a final protein concentration of about 280 mg/mL. Solutions of BGG in 50 mM histidine HCl with excipient were formulated in 20 mL vials and allowed to shake at 100 rpm on an orbital shaker table overnight. The solutions were then transferred to 2 mL microcentrifuge tubes and centrifuged for ten minutes at 2300 rpm in an IEC MicroMax microcentrifuge to remove entrained air prior to viscosity measurement.

Viscosity measurements of formulations prepared as described above were made with a DV-IIT LV cone and plate viscometer (Brookfield Engineering, Middleboro, MA). The viscometer was equipped with a CP-40 cone and was operated at 3 rpm and 25 degrees C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty-second measurement collection period. The three data points collected were then averaged and recorded as the viscosity for the sample. Viscosities of solutions with excipient were normalized to the viscosity of the model protein solution without excipient. The normalized viscosity is the ratio of the viscosity of the model protein solution with excipient to the viscosity of the model protein solution with no excipient.

TABLE 4

| Test Number | Excipient Added | Excipient Concentration (mg/mL) | Normalized Viscosity (cP) | Viscosity Reduction |
|---|---|---|---|---|
| 9.1 | DMCHA-HCl | 120 | 0.44 | 56% |
| 9.2 | Niacinamide | 50 | 0.51 | 49% |
| 9.3 | Isonicotinamide | 50 | 0.48 | 52% |
| 9.4 | Tyramine HCl | 70 | 0.41 | 59% |
| 9.5 | Histamine HCl | 50 | 0.41 | 59% |
| 9.6 | Imidazole HCl | 100 | 0.43 | 57% |
| 9.7 | 2-methyl-2-imidazoline HCl | 60 | 0.43 | 57% |
| 9.8 | 1-butyl-3-methylimidazolium chloride | 100 | 0.48 | 52% |
| 9.9 | Procaine HCl | 50 | 0.53 | 47% |
| 9.10 | 3-aminopyridine | 50 | 0.51 | 49% |
| 9.11 | 2,4,6-trimethylpyridine | 50 | 0.49 | 51% |
| 9.12 | 3-pyridine methanol | 50 | 0.53 | 47% |
| 9.13 | Nicotinamide adenine dinucleotide | 20 | 0.56 | 44% |
| 9.15 | Sodium phenylpyruvate | 55 | 0.57 | 43% |
| 9.16 | 2-Pyrrolidinone | 60 | 0.68 | 32% |
| 9.17 | Morpholine HCl | 50 | 0.60 | 40% |
| 9.18 | Agmatine sulfate | 55 | 0.77 | 23% |
| 9.19 | 1-butyl-3-methylimidazolium iodide | 60 | 0.66 | 34% |
| 9.21 | L-Anserine nitrate | 50 | 0.79 | 21% |
| 9.22 | 1-hexyl-3-methylimidazolium chloride | 65 | 0.89 | 11% |
| 9.23 | N,N-diethyl nicotinamide | 50 | 0.67 | 33% |
| 9.24 | Nicotinic acid, sodium salt | 100 | 0.54 | 46% |
| 9.25 | Biotin | 20 | 0.69 | 31% |

Example 10: Preparation of Formulations Containing Excipient Combinations and Test Protein Formulations were prepared using a primary excipient compound, a secondary excipient compound and a test protein, where the test protein was intended to simulate either a therapeutic protein that would be used in a therapeutic formulation, or anon-therapeutic protein that would be used in a non-therapeutic formulation. The primary excipient compounds were selected from compounds having both anionic and aromatic functionality, as listed below in Table 5. The secondary excipient compounds were selected from compounds having either nonionic or cationic charge at pH 6 and either imidazoline or benzene rings, as listed below in Table 5. Formulations of these excipients were prepared in 50 mM histidine hydrochloride buffer solution for viscosity measurement in the following way. Histidine hydrochloride was first prepared by dissolving 1.94 g histidine (Sigma-Aldrich, St. Louis, MO) in distilled water and adjusting the pH to about 6.0 with 1 M hydrochloric acid (Sigma-Aldrich, St. Louis, MO) and then diluting to a final volume of 250 mL with distilled water in a volumetric flask. The individual primary or secondary excipient compounds were then dissolved in 50 mM histidine HCl. Combinations of primary and secondary excipients were dissolved in 50 mM histidine HCl and the resulting solution pH adjusted with small amounts of concentrated sodium hydroxide or hydrochloric acid to achieve pH 6 prior to dissolution of the model protein. Once excipient solutions had been prepared as described above, the test protein (bovine gamma globulin (BGG) (Sigma-Aldrich, St. Louis, MO)) was dissolved into each test solution at a ratio to achieve a final protein concentration of about 280 mg/mL. Solutions of BGG in 50 mM histidine HCl with excipient were formulated in 20 mL vials and allowed to shake at 100 rpm on an orbital shaker table overnight. The solutions were then transferred to 2 mL microcentrifuge tubes and centrifuged for ten minutes at 2300 rpm in an IEC MicroMax microcentrifuge to remove entrained air prior to viscosity measurement.

Viscosity measurements of formulations prepared as described above were made with a DV-IIT LV cone and plate viscometer (Brookfield Engineering, Middleboro, MA). The viscometer was equipped with a CP-40 cone and was operated at 3 rpm and 25 degrees C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and a subsequent twenty-second measurement collection period. The three data points collected were then averaged and recorded as the viscosity for the sample. Viscosities of solutions with excipient were normalized to the viscosity of the model protein solution without excipient, and summarized in Table 5 below. The normalized viscosity is the ratio of the viscosity of the model protein solution with excipient to the viscosity of the model protein solution with no excipient. The example shows that a combination of primary and secondary excipients can give a better result than a single excipient.

TABLE 5

| | Primary Excipient | | Secondary Excipient | | |
|---|---|---|---|---|---|
| Test Number | Name | Concentration (mg/mL) | Name | Concentration (mg/mL) | Normalized Viscosity |
| 10.1 | Salicylic Acid | 30 | None | 0 | 0.79 |
| 10.2 | Salicylic Acid | 25 | Imidazole | 4 | 0.59 |
| 10.3 | 4-hydroxybenzoic acid | 30 | None | 0 | 0.61 |
| 10.4 | 4-hydroxybenzoic acid | 25 | Imidazole | 5 | 0.57 |

TABLE 5-continued

| Test Number | Primary Excipient Name | Concentration (mg/mL) | Secondary Excipient Name | Concentration (mg/mL) | Normalized Viscosity |
|---|---|---|---|---|---|
| 10.5 | 4-hydroxybenzene sulfonic acid | 31 | None | 0 | 0.59 |
| 10.6 | 4-hydroxybenzene sulfonic acid | 26 | Imidazole | 5 | 0.70 |
| 10.7 | 4-hydroxybenzene sulfonic acid | 25 | Caffeine | 5 | 0.69 |
| 10.8 | None | 0 | Caffeine | 10 | 0.73 |
| 10.9 | None | 0 | Imidazole | 5 | 0.75 |

Example 11: Preparation of Formulations Containing Excipient Combinations and Test Protein Formulations were prepared using a primary excipient compound, a secondary excipient compound and a test protein, where the test protein was intended to simulate a therapeutic protein that would be used in a therapeutic formulation, or anon-therapeutic protein that would be used in a anon-therapeutic formulation. The primary excipient compounds were selected from compounds having both anionic and aromatic functionality, as listed below in Table 6. The secondary excipient compounds were selected from compounds having either nonionic or cationic charge at pH 6 and either imidazoline or benzene rings, as listed below in Table 6. Formulations of these excipients were prepared in distilled water for viscosity measurement in the following way. Combinations of primary and secondary excipients were dissolved in distilled water and the resulting solution pH adjusted with small amounts of concentrated sodium hydroxide or hydrochloric acid to achieve pH 6 prior to dissolution of the model protein. Once excipient solutions in distilled water had been prepared, the test protein (bovine gamma globulin (BGG) (Sigma-Aldrich, St. Louis, MO)) was dissolved at a ratio to achieve a final protein concentration of about 280 mg/mL. Solutions of BGG in distilled water with excipient were formulated in 20 mL vials and allowed to shake at 100 rpm on an orbital shaker table overnight. The solutions were then transferred to 2 mL microcentrifuge tubes and centrifuged for ten minutes at 2300 rpm in an IEC MicroMax microcentrifuge to remove entrained air prior to viscosity measurement.

Viscosity measurements of formulations prepared as described above were made with a DV-IIT LV cone and plate viscometer (Brookfield Engineering, Middleboro, MA). The viscometer was equipped with a CP-40 cone and was operated at 3 rpm and 25 degrees C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and a subsequent twenty-second measurement collection period. The three data points collected were then averaged and recorded as the viscosity for the sample. Viscosities of solutions with excipient were normalized to the viscosity of the model protein solution without excipient, and summarized in Table 6 below. The normalized viscosity is the ratio of the viscosity of the model protein solution with excipient to the viscosity of the model protein solution with no excipient. The example shows that a combination of primary and secondary excipients can give a better result than a single excipient.

TABLE 6

| Test Number | Primary Excipient Name | Concentration (mg/mL) | Secondary Excipient Name | Concentration (mg/mL) | Normalized Viscosity |
|---|---|---|---|---|---|
| 11.1 | Salicylic Acid | 20 | None | 0 | 0.96 |
| 11.2 | Salicylic Acid | 20 | Caffeine | 5 | 0.71 |
| 11.3 | Salicylic Acid | 20 | Niacinamide | 5 | 0.76 |
| 11.4 | Salicylic Acid | 20 | Imidazole | 5 | 0.73 |

Example 12: Preparation of Formulations Containing Excipient Compounds and PEG Materials: All materials were purchased from Sigma-Aldrich, St. Louis, MO Formulations were prepared using an excipient compound and PEG, where the PEG was intended to simulate a therapeutic PEGylated protein that would be used in a therapeutic formulation. Such formulations were prepared by mixing equal volumes of a solution of PEG with a solution of the excipient. Both solutions were prepared in a Tris buffer consisting of 10 mM Tris, 135 mM NaCl, and 1 mM trans-cinnamic acid at pH of 7.3.

The PEG solution was prepared by mixing 3 g of Poly(ethylene oxide) average Mw~1,000,000 (Aldrich Catalog #372781) with 97 g of the Tris buffer solution. The mixture was stirred overnight for complete dissolution.

An example of the excipient solution preparation is as follows: An approximately 80 mg/mL solution of citric acid in the Tris buffer was prepared by dissolving 0.4 g of citric acid (Aldrich cat. #251275) in 5 mL of the Tris buffer solution and adjusted the pH to 7.3 with minimum amount of 10 M NaOH solution.

The PEG excipient solution was prepared by mixing 0.5 mL of the PEG solution with 0.5 mL of the excipient solution and mixed by using a vortex for a few seconds. A control sample was prepared by mixing 0.5 mL of the PEG solution with 0.5 mL of the Tris buffer solution.

Example 13: Viscosity Measurements of Formulations Containing Excipient Compounds and PEG Viscosity measurements of the formulations prepared were made with a DV-IIT LV cone and plate viscometer (Brookfield Engineering, Middleboro, MA). The viscometer was equipped with a CP-40 cone and was operated at 3 rpm and 25 degrees C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty second measurement collection period. The three data points collected were then averaged and recorded as the viscosity for the sample.

The results presented in Table 7 show the effect of the added excipient compounds in reducing viscosity.

TABLE 7

| Test Number | Excipient | Excipient Concentration (mg/mL) | Viscosity (cP) | Viscosity Reduction |
|---|---|---|---|---|
| 13.1 | None | 0 | 104.8 | 0% |
| 13.2 | Citric acid Na salt | 40 | 56.8 | 44% |
| 13.3 | Citric acid Na salt | 20 | 73.3 | 28% |
| 13.4 | glycerol phosphate | 40 | 71.7 | 30% |
| 13.5 | glycerol phosphate | 20 | 83.9 | 18% |
| 13.6 | Ethylene diamine | 40 | 84.7 | 17% |
| 13.7 | Ethylene diamine | 20 | 83.9 | 15% |
| 13.8 | EDTA/K salt | 40 | 67.1 | 36% |
| 13.9 | EDTA/K salt | 20 | 76.9 | 27% |
| 13.10 | EDTA/Na salt | 40 | 68.1 | 35% |
| 13.11 | EDTA/Na salt | 20 | 77.4 | 26% |
| 13.12 | D-Gluconic acid/K salt | 40 | 80.32 | 23% |
| 13.13 | D-Gluconic acid/K salt | 20 | 88.4 | 16% |
| 13.14 | D-Gluconic acid/Na salt | 40 | 81.24 | 23% |
| 13.15 | D-Gluconic acid/Na salt | 20 | 86.6 | 17% |
| 13.16 | lactic acid/K salt | 40 | 80.42 | 23% |
| 13.17 | lactic acid/K salt |  | 85.1 | 19% |
| 13.18 | lactic acid/Na salt | 40 | 86.55 | 17% |
| 13.19 | lactic acid/Na salt | 20 | 87.2 | 17% |
| 13.20 | etidronic acid/K salt | 24 | 71.91 | 31% |
| 13.21 | etidronic acid/K salt | 12 | 80.5 | 23% |
| 13.22 | etidronic acid/Na salt | 24 | 71.6 | 32% |
| 13.23 | etidronic acid/Na salt | 12 | 79.4 | 24% |

Example 14: Preparation of PEGylated BSA with 1 PEG Chain Per BSA Molecule

To a beaker was added 200 mL of a phosphate buffered saline (Aldrich Cat. #P4417) and 4 g of BSA (Aldrich Cat. #A7906) and mixed with a magnetic bar. Next 400 mg of methoxy polyethylene glycol maleimide, MW=5,000, (Aldrich Cat. #63187) was added. The reaction mixture was allowed to react overnight at room temperature. The following day, 20 drops of HCl 0.1 M were added to stop the reaction. The reaction product was characterized by SDS-Page and SEC which clearly showed the PEGylated BSA. The reaction mixture was placed in an Amicon centrifuge tube with a molecular weight cutoff (MWCO) of 30,000 and concentrated to a few milliliters. Next the sample was diluted 20 times with a histidine buffer, 50 mM at a pH of approximately 6, followed by concentrating until a high viscosity fluid was obtained. The final concentration of the protein solution was obtained by measuring the absorbance at 280 nm and using a coefficient of extinction for the BSA of 0.6678. The results indicated that the final concentration of BSA in the solution was 342 mg/mL.

Example 15: Preparation of PEGylated BSA with Multiple PEG Chains Per BSA Molecule A 5 mg/mL solution of BSA (Aldrich A7906) in phosphate buffer, 25 mM at pH of 7.2, was prepared by mixing 0.5 g of the BSA with 100 mL of the buffer. Next 1 g of a methoxy PEG propionaldehyde Mw=20,000 (JenKem Technology, Plano, TX 75024) was added followed by 0.12 g of sodium cyanoborohydride (Aldrich 156159). The reaction was allowed to proceed overnight at room temperature. The following day the reaction mixture was diluted 13 times with a Tris buffer (10 mM Tris, 135 mM NaCl at pH=7.3) and concentrated using Amicon centrifuge tubes MWCO of 30,000 until a concentration of approximately 150 mg/mL was reached.

Example 16: Preparation of PEGylated Lysozyme with Multiple PEG Chains Per Lysozyme Molecule A 5 mg/mL solution of lysozyme (Aldrich L6876) in phosphate buffer, 25 mM at pH of 7.2, was prepared by mixing 0.5 g of the lysozyme with 100 mL of the buffer. Next 1 g of a methoxy PEG propionaldehyde Mw=5,000 (JenKem Technology, Plano, TX 75024) was added followed by 0.12 g of Sodium cyanoborohydride (Aldrich 156159). The reaction was allowed to proceed overnight at room temperature. The following day the reaction mixture was diluted 49 times with the phosphate buffer, 25 mM at pH of 7.2, and concentrated using Amicon centrifuge tubes MWCO of 30,000. The final concentration of the protein solution was obtained by measuring the absorbance at 280 nm and using a coefficient of extinction for the lysozyme of 2.63. The final concentration of lysozyme in the solution was 140 mg/mL.

Example 17: Effect of Excipients on Viscosity of PEGylated BSA with 1 PEG Chain Per BSA Molecule Formulations of PEGylated BSA (from Example 14 above) with excipients were prepared by adding 6 or 12 milligrams of the excipient salt to 0.3 mL of the PEGylated BSA solution. The solution was mixed by gently shaking and the viscosity was measured by a RheoSense microVisc equipped with an A10 channel (100 micron depth) at a shear rate of 500 sec$^{-1}$. The viscometer measurements were completed at ambient temperature.

The results presented in Table 8 shows the effect of the added excipient compounds in reducing viscosity.

TABLE 8

| Test Number | Excipient | Excipient Concentration (mg/mL) | Viscosity (cP) | Viscosity Reduction |
|---|---|---|---|---|
| 17.1 | None | 0 | 228.6 | 0% |
| 17.2 | Alpha-Cyclodextrin sulfated Na salt | 20 | 151.5 | 34% |
| 17.3 | K acetate | 40 | 89.5 | 60% |

Example 18: Effect of Excipients on Viscosity of PEGylated BSA with Multiple PEG Chains Per BSA Molecule A formulations of PEGylated BSA (from Example 15 above) with citric acid Na salt as excipient was prepared by adding 8 milligrams of the excipient salt to 0.2 mL of the PEGylated BSA solution. The solution was mixed by gently shaking and the viscosity was measured by a RheoSense microVisc equipped with an A10 channel (100 micron depth) at a shear rate of 500 sec$^{-1}$. The viscometer measurements were completed at ambient temperature. The results presented in Table 9 shows the effect of the added excipient compounds in reducing viscosity.

TABLE 9

| Test Number | Excipient Added | Excipient Concentration (mg/mL) | Viscosity (cP) | Viscosity Reduction |
|---|---|---|---|---|
| 18.1 | None | 0 | 56.8 | 0% |
| 18.2 | Citric acid Na salt | 40 | 43.5 | 23% |

Example 19: Effect of Excipients on Viscosity of PEGylated Lysozyme with Multiple PEG Chains Per Lysozyme Molecule A formulation of PEGylated lysozyme (from Example 16 above) with potassium acetate as excipient was prepared by adding 6 milligrams of the excipient salt to 0.3 mL of the PEGylated lysozyme solution. The solution was mixed by gently shaking and the viscosity was measured by a RheoSense microVisc equipped with an A10 channel (100 micron depth) at a shear rate of 500 sec$^{-1}$. The viscometer measurements were completed at ambient temperature. The results presented in the next table shows the benefit of the added excipient compounds in reducing viscosity.

TABLE 10

| Test Number | Excipient | Excipient Concentration (mg/mL) | Viscosity (cP) | Viscosity Reduction |
|---|---|---|---|---|
| 19.1 | None | 0 | 24.6 | 0% |
| 19.2 | K acetate | 20 | 22.6 | 8% |

Example 20: Protein Formulations Containing Excipient Combinations

Formulations were prepared using an excipient compound or a combination of two excipient compounds and a test protein, where the test protein was intended to simulate a therapeutic protein that would be used in a therapeutic formulation. These formulations were prepared in 20 mM histidine buffer with different excipient compounds for viscosity measurement in the following way. Excipient combinations were dissolved in 20 mM histidine (Sigma-Aldrich, St. Louis, MO) and the resulting solution pH adjusted with small amounts of concentrated sodium hydroxide or hydrochloric acid to achieve pH 6 prior to dissolution of the model protein. Excipient compounds for this Example are listed below in Table 11. Once excipient solutions had been prepared, the test protein (bovine gamma globulin (BGG) (Sigma-Aldrich, St. Louis, MO)) was dissolved at a ratio to achieve a final protein concentration of about 280 mg/mL. Solutions of BGG in the excipient solutions were formulated in 5 mL sterile polypropylene tubes and allowed to shake at 80-100 rpm on an orbital shaker table overnight. The solutions were then transferred to 2 mL microcentrifuge tubes and centrifuged for about ten minutes at 2300 rpm in an IEC MicroMax microcentrifuge to remove entrained air prior to viscosity measurement.

Viscosity measurements of formulations prepared as described above were made with a DV-IIT LV cone and plate viscometer (Brookfield Engineering, Middleboro, MA). The viscometer was equipped with a CP-40 cone and was operated at 3 rpm and 25 degrees Centigrade. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty second measurement collection period. The three data points collected were then averaged and recorded as the viscosity for the sample. Viscosities of solutions with excipient were normalized to the viscosity of the model protein solution without excipient, and the results are shown in Table 11 below. The normalized viscosity is the ratio of the viscosity of the model protein solution with excipient to the viscosity of the model protein solution with no excipient.

TABLE 11

| | Excipient A | | Excipient B | | |
|---|---|---|---|---|---|
| Test # | Name | Conc. (mg/mL) | Name | Conc. (mg/mL) | Normalized Viscosity |
| 20.1 | None | 0 | None | 0 | 1.00 |
| 20.2 | Aspartame | 10 | None | 0 | 0.83 |

TABLE 11-continued

| Test # | Excipient A Name | Conc. (mg/mL) | Excipient B Name | Conc. (mg/mL) | Normalized Viscosity |
|---|---|---|---|---|---|
| 20.3 | Saccharin | 60 | None | 0 | 0.51 |
| 20.4 | Acesulfame K | 80 | None | 0 | 0.44 |
| 20.5 | Theophylline | 10 | None | 0 | 0.84 |
| 20.6 | Saccharin | 30 | None | 0 | 0.58 |
| 20.7 | Acesulfame K | 40 | None | 0 | 0.61 |
| 20.8 | Caffeine | 15 | Taurine | 15 | 0.82 |
| 20.9 | Caffeine | 15 | Tyramine | 15 | 0.67 |

Example 21: Protein Formulations Containing Excipients to Reduce Viscosity and Injection Pain Formulations were prepared using an excipient compound, a second excipient compound, and a test protein, where the test protein was intended to simulate a therapeutic protein that would be used in a therapeutic formulation. The first excipient compound, Excipient A, was selected from a group of compounds having local anesthetic properties. The first excipient, Excipient A and the second excipient, Excipient B are listed in Table 12. These formulations were prepared in 20 mM histidine buffer using Excipient A and Excipient B in the following way, so that their viscosities could be measured. Excipients in the amounts disclosed in Table 12 were dissolved in 20 mM histidine (Sigma-Aldrich, St Louis, MO) and the resulting solutions were pH adjusted with small amounts of concentrated sodium hydroxide or hydrochloric acid to achieve pH 6 prior to dissolution of the model protein. Once excipient solutions had been prepared, the test protein (bovine gamma globulin (BGG) (Sigma-Aldrich, St. Louis, MO)) was dissolved in the excipient solution at a ratio to achieve a final protein concentration of about 280 mg/mL. Solutions of BGG in the excipient solutions were formulated in 5 mL sterile polypropylene tubes and allowed to shake at 80-100 rpm on an orbital shaker table overnight. BGG-excipient solutions were then transferred to 2 mL microcentrifuge tubes and centrifuged for about ten minutes at 2300 rpm in an IEC MicroMax microcentrifuge to remove entrained air prior to viscosity measurement.

Viscosity measurements of the formulations prepared as described above were made with a DV-IIT LV cone and plate viscometer (Brookfield Engineering, Middleboro, MA). The viscometer was equipped with a CP-40 cone and was operated at 3 rpm and 25 degrees Centigrade. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty second measurement collection period. The three data points collected were then averaged and recorded as the viscosity for the sample. Viscosities of solutions with excipient were normalized to the viscosity of the model protein solution without excipient, and the results are shown in Table 12 below. The normalized viscosity is the ratio of the viscosity of the model protein solution with excipient to the viscosity of the model protein solution with no excipient.

TABLE 12

| Test # | Excipient A Name | Conc. (mg/mL) | Excipient B Name | Conc. (mg/mL) | Normalized Viscosity |
|---|---|---|---|---|---|
| 21.1 | None | 0 | None | 0 | 1.00 |
| 21.2 | Lidocaine | 45 | None | 0 | 0.73 |
| 21.3 | Lidocaine | 23 | None | 0 | 0.74 |
| 21.4 | Lidocaine | 10 | Caffeine | 15 | 0.71 |
| 21.5 | Procaine HCl | 40 | None | 0 | 0.64 |
| 21.6 | Procaine HCl | 20 | Caffeine | 15 | 0.69 |

Example 22: Formulations Containing Excipient Compounds and PEG

Formulations were prepared using an excipient compound and PEG, where the PEG was intended to simulate a therapeutic PEGylated protein that would be used in a therapeutic formulation, and where the excipient compounds were provided in the amounts as listed in Table 13. These formulations were prepared by mixing equal volumes of a solution of PEG with a solution of the excipient. Both solutions were prepared in DI-Water.

The PEG solution was prepared by mixing 16.5 g of poly(ethylene oxide) average Mw~100,000 (Aldrich Catalog #181986) with 83.5 g of DI water. The mixture was stirred overnight for complete dissolution.

The excipient solutions were prepared by this general method and as detailed in Table 13 below: An approximately 20 mg/mL solution of potassium phosphate tribasic (Aldrich Catalog #P5629) in DI-water was prepared by dissolving 0.05 g of potassium phosphate in 5 mL of DI-water. The PEG excipient solution was prepared by mixing 0.5 mL of the PEG solution with 0.5 mL of the excipient solution and mixed by using a vortex for a few seconds. A control sample was prepared by mixing 0.5 mL of the PEG solution with 0.5 mL of DI-water. Viscosity was measured and results are recorded in Table 13 below.

TABLE 13

| Test Number | Excipient | Excipient Concentration (mg/mL) | Viscosity (cP) | Viscosity Reduction (%) |
|---|---|---|---|---|
| 22.1 | None | 0 | 79.7 | 0 |
| 22.2 | Citric acid Na salt | 10 | 74.9 | 6.0 |
| 22.3 | Potassium phosphate | 10 | 72.3 | 9.3 |
| 22.4 | Citric acid Na salt/Potassium phosphate | 10/10 | 69.1 | 13.3 |
| 22.5 | Sodium sulfate | 10 | 75.1 | 5.8 |
| 22.6 | Citric acid Na salt/Sodium sulfate | 10/10 | 70.4 | 11.7 |

Example 23: Improved Processing of Protein Solutions with Excipients

Two BGG solutions were prepared by mixing 0.25 g of solid BGG (Aldrich catalogue number G5009) with 4 ml of a buffer solution. For Sample A: Buffer solution was 20 mM histidine buffer (pH=6.0). For sample B: Buffer solution was 20 mM histidine buffer containing 15 mg/ml of caffeine (pH=6). The dissolution of the solid BGG was carried out by placing the samples in an orbital shaker set at 100 rpm. The buffer sample containing caffeine excipient was observed to dissolve the protein faster. For the sample with the caffeine excipient (Sample B) complete dissolution of the BGG was achieved in 15 minutes. For the sample without the caffeine (Sample A) the dissolution needed 35 minutes.

Next the samples were placed in 2 separate Amicon Ultra 4 Centrifugal Filter Unit with a 30,000 molecular weight cut off and the samples were centrifuged at 2,500 rpm at 10 minute intervals. The filtrate volume recovered after each 10 minute centrifuge run was recorded. The results in Table 14 show the faster recovery of the filtrate for Sample B. In addition, Sample B kept concentrating with every additional run but Sample A reached a maximum concentration point and further centrifugation did not result in further sample concentration.

TABLE 14

| Centrifuge time (min) | Sample A filtrate collected (mL) | Sample B filtrate collected (mL) |
| --- | --- | --- |
| 10 | 0.28 | 0.28 |
| 20 | 0.56 | 0.61 |
| 30 | 0.78 | 0.88 |
| 40 | 0.99 | 1.09 |
| 50 | 1.27 | 1.42 |
| 60 | 1.51 | 1.71 |
| 70 | 1.64 | 1.99 |
| 80 | 1.79 | 2.29 |
| 90 | 1.79 | 2.39 |
| 100 | 1.79 | 2.49 |

Example 24: Protein Formulations Containing Multiple Excipients

This example shows how the combination of caffeine and arginine as excipients has a beneficial effect on decreasing viscosity of a BGG solution. Four BGG solutions were prepared by mixing 0.18 g of solid BGG (Aldrich catalogue number G5009) with 0.5 mL of a 20 mM Histidine buffer at pH 6. Each buffer solution contained different excipient or combination of excipients as described in the table below. The viscosity of the solutions was measured as described in previous examples. The results show that the hindered amine excipient, caffeine, can be combined with known excipients such as arginine, and the combination has better viscosity reduction properties than the individual excipients by themselves.

TABLE 15

| Sample | Excipient(s) added | Viscosity (cP) | Viscosity Reduction (%) |
| --- | --- | --- | --- |
| A | None | 130.6 | 0 |
| B | Caffeine (10 mg/ml) | 87.9 | 33 |
| C | Caffeine (10 mg/ml)/Arginine (25 mg/ml) | 66.1 | 49 |
| D | Arginine (25 mg/ml) | 76.7 | 41 |

Arginine was added to 280 mg/mL solutions of BGG in histidine buffer at pH 6. At levels above 50 mg/mL, adding more arginine did not decrease viscosity further, as shown in Table 16.

TABLE 16

| Arginine added (mg/mL) | Viscosity (cP) | Viscosity reduction (%) |
| --- | --- | --- |
| 0 | 79.0 | 0% |
| 53 | 40.9 | 48% |
| 79 | 46.1 | 42% |
| 105 | 47.8 | 40% |
| 132 | 49.0 | 38% |
| 158 | 48.0 | 39% |
| 174 | 50.3 | 36% |
| 211 | 51.4 | 35% |

Caffeine was added to 280 mg/mL solutions of BGG in histidine buffer at pH 6. At levels above 10 mg/ml, adding more caffeine did not decrease viscosity further, as shown in Table 17.

TABLE 17

| Caffeine added (mg/mL) | Viscosity (cP) | Viscosity reduction (%) |
| --- | --- | --- |
| 0 | 79 | 0% |
| 10 | 60 | 31% |
| 15 | 62 | 23% |
| 22 | 50 | 45% |

Example 25: Preparation of Solutions of Co-Solutes in Deionized Water

Compounds used as co-solutes to increase caffeine solubility in water were obtained from Sigma-Aldrich (St. Louis, MO) and included niacinamide, proline, procaine HCl, ascorbic acid, 2,5-dihydroxybenzoic acid, lidocaine, saccharin, acesulfame K, tyramine, and aminobenzoic acid. Solutions of each co-solute were prepared by dissolving dry solid in deionized water and in some cases adjusting the pH to a value between pH of about 6 and pH of about 8 with 5 M hydrochloric acid or 5 M sodium hydroxide as necessary. Solutions were then diluted to a final volume of either 25 mL or 50 mL using a Class A volumetric flask and concentration recorded based on the mass of compound dissolved and the final volume of the solution. Prepared solutions were used either neat or diluted with deionized water.

Example 26: Caffeine Solubility Testing

The impact of different co-solutes on the solubility of caffeine at ambient temperature (about 23° C.) was assessed in the following way. Dry caffeine powder (Sigma-Aldrich, St. Louis, MO) was added to 20 mL glass scintillation vials and the mass of caffeine recorded. 10 mL of a co-solute solution prepared in accordance with Example 25 was added to the caffeine powder in certain cases (as recorded in Table 18); in other cases (as recorded in Table 18), a blend of a co-solute solution and deionized water was added to the caffeine powder, maintaining a final addition volume of 10 mL. The volume contribution of the dry caffeine powder was assumed to be negligible in any of these mixtures. A small magnetic stir bar was added to the vial, and the solution was allowed to mix vigorously on a stir plate for about 10 minutes. After about 10 minutes the vial was observed for dissolution of the dry caffeine powder, and the results are given in Table 18 below. These observations indicated that niacinamide, procaine HCl, 2,5-dihydroxybenzoic acid sodium salt, saccharin sodium salt, and tyramine chloride salt all enabled dissolution of caffeine to at least about four times the reported caffeine solubility limit (~16 mg/mL at room temperature according to Sigma-Aldrich).

TABLE 18

| Test No. | Co-solute Name | Conc. (mg/mL) | Caffeine (mg/mL) | Observation |
|---|---|---|---|---|
| 26.1 | Proline | 100 | 50 | DND |
| 26.2 | Niacinamide | 100 | 50 | CD |
| 26.3 | Niacinamide | 100 | 60 | CD |
| 26.4 | Niacinamide | 100 | 75 | CD |
| 26.5 | Niacinamide | 100 | 85 | CD |
| 26.6 | Niacinamide | 100 | 100 | CD |
| 26.7 | Niacinamide | 80 | 85 | CD |
| 26.8 | Niacinamide | 50 | 80 | CD |
| 26.9 | Procaine HCl | 100 | 85 | CD |
| 26.10 | Procaine HCl | 50 | 80 | CD |
| 26.11 | Niacinamide | 30 | 80 | DND |
| 26.12 | Procaine HCl | 30 | 80 | DND |
| 26.13 | Niacinamide | 40 | 80 | MD |
| 26.14 | Procaine HCl | 40 | 80 | DND |
| 26.15 | Ascorbic acid, Na | 50 | 80 | DND |
| 26.16 | Ascorbic acid, Na | 100 | 80 | DND |
| 26.17 | 2,5 DHBA, Na | 40 | 80 | CD |
| 26.18 | 2,5 DHBA, Na | 20 | 80 | MD |
| 26.19 | Lidocaine HCl | 40 | 80 | DND |
| 26.20 | Saccharin, Na | 90 | 80 | CD |
| 26.21 | Acesulfame K | 80 | 80 | DND |
| 26.22 | Tyramine HCl | 60 | 80 | CD |
| 26.23 | Na Aminobenzoate | 46 | 80 | DND |
| 26.24 | Saccharin, Na | 45 | 80 | DND |
| 26.25 | Tyramine HCl | 30 | 80 | DND |

CD = completely dissolved;
MD = mostly dissolved;
DND = did not dissolve

Example 27: Impact of Higher Caffeine Concentrations on Protein Formulations

Formulations were prepared using a primary excipient compound, a secondary excipient compound and a test protein, where the test protein was intended to simulate a therapeutic protein that would be used in a therapeutic formulation. The primary excipient compounds were selected from compounds having both low solubility and demonstrated viscosity reduction. The secondary excipient compounds were selected from compounds having higher solubility and either pyridine or benzene rings. Such formulations were prepared in 20 mM histidine buffer with different excipient compounds for viscosity measurement in the following way: excipient combinations were dissolved in 20 mM histidine buffer solution and the resulting solution pH adjusted with small amounts of concentrated sodium hydroxide or hydrochloric acid to achieve pH 6 prior to dissolution of the model protein. In certain experiments, the primary excipient was added in amounts greatly exceeding its room temperature solubility limit as reported in literature. Once the excipient solutions had been prepared, the test protein (bovine gamma globulin (BGG, Sigma-Aldrich, St. Louis, MO)) was dissolved at a ratio to achieve a final protein concentration of about 280 mg/mL. Solutions of BGG in the excipient solutions were formulated in 20 mL vials and allowed to shake at 100 rpm on an orbital shaker table overnight. The solutions were then transferred to 2 mL microcentrifuge tubes and centrifuged for ten minutes at 2300 rpm in an IEC MicroMax microcentrifuge to remove entrained air prior to viscosity measurement.

Viscosity measurements of formulations prepared as described above were made with a DV-IIT LV cone and plate viscometer (Brookfield Engineering, Middleboro, MA). The viscometer was equipped with a CP-40 cone and was operated at 3 rpm and 25 degrees Centigrade. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty second measurement collection period. The three data points collected were then averaged and recorded as the viscosity for the sample, as shown in Table 19 below. Viscosities of solutions with excipient were normalized to the viscosity of the model protein solution without excipient. The normalized viscosity is the ratio of the viscosity of the model protein solution with excipient to the viscosity of the model protein solution with no excipient.

TABLE 19

| Test No. | Primary Excipient Name | Conc. (mg/mL) | Secondary Excipient Name | (mg/mL) | Normalized Viscosity |
|---|---|---|---|---|---|
| 27.1 | Caffeine | 15 | None | 0 | 0.75 |
| 27.2 | Caffeine | 15 | Saccharin | 14 | 0.62 |
| 27.3 | Caffeine | 15 | Procaine HCl | 20 | 0.61 |
| 27.4 | Caffeine | 60 | Niacinamide | 50 | 0.61 |
| 27.5 | Caffeine | 60 | Procaine HCl | 50 | 0.60 |
| 27.6 | Caffeine | 60 | Saccharin | 50 | 0.66 |

Example 28: Improved Stability of Adalimumab Solutions with Caffeine as Excipient The stability of adalimumab solutions with and without caffeine excipient was evaluated after exposing samples to 2 different stress conditions: agitation and freeze-thaw. The adalimumab drug formulation Humira® was used, having properties described in more detail in Example 32. The Humira® sample was concentrated to 200 mg/ml adalimumab concentration in the original buffer solution as described in Example 32; this concentrated sample is designated "Sample 1". A second sample was prepared with ~200 mg/mL of adalimumab and 15 mg/mL of added caffeine as described in Example 33; this concentrated sample with added caffeine is designated "Sample 2". Both samples were diluted to a final concentration of 1 mg/ml adalimumab with the diluents as follows: Sample 1 diluent is the original buffer solution, and Sample 2 diluent is a 20 mM histidine, 15 mg/ml caffeine, pH=5. Both Humira® dilutions were filtered through a 0.22µ syringe filter. For every diluted sample, 3 batches of 300 µl each were prepared in a 2 ml Eppendorf tube in a laminar flow hood. The samples were submitted to the following stress conditions: for agitation, samples were placed in an orbital shaker at 300 rpm for 91 hours; for freeze-thaw, samples were cycled 7 times from −17 to 30 C for an average of 6 hours per condition. Table 20 describes the samples prepared.

TABLE 20

| Sample # | Excipient added | Stress condition |
|---|---|---|
| 1-C | None | None |
| 1-A | None | Agitation |
| 1-FT | None | Freeze-Thaw |
| 2-C | 15 mg/mL caffeine | None |

TABLE 20-continued

| Sample # | Excipient added | Stress condition |
|---|---|---|
| 2-A | 15 mg/mL caffeine | Agitation |
| 2-FT | 15 mg/mL caffeine | Freeze-Thaw |

Evaluation of Stability by Dynamic Light Scattering (DLS)

Figure 2:
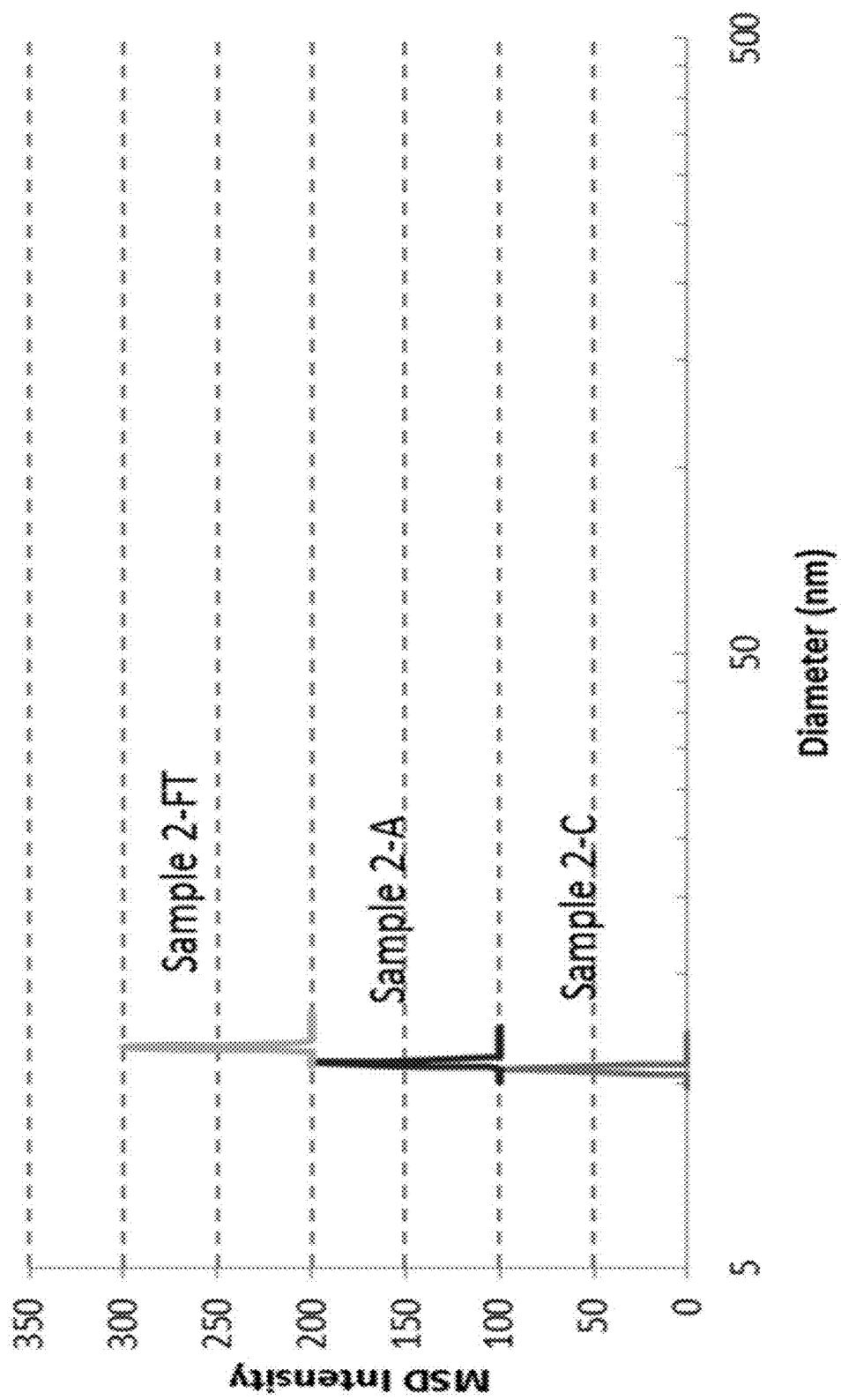
FIG. 2 shows a graph measuring sample diameter vs. multimodal size distribution for several molecular populations, as evaluated by Dynamic Light Scattering. The data curves in FIG. 2 have a baseline offset to allow comparison: the curve for Sample 2-A is offset by 100 intensity units and the curve for Sample 2-FT is offset by 200 intensity units in the Y-axis.
Figure 3:
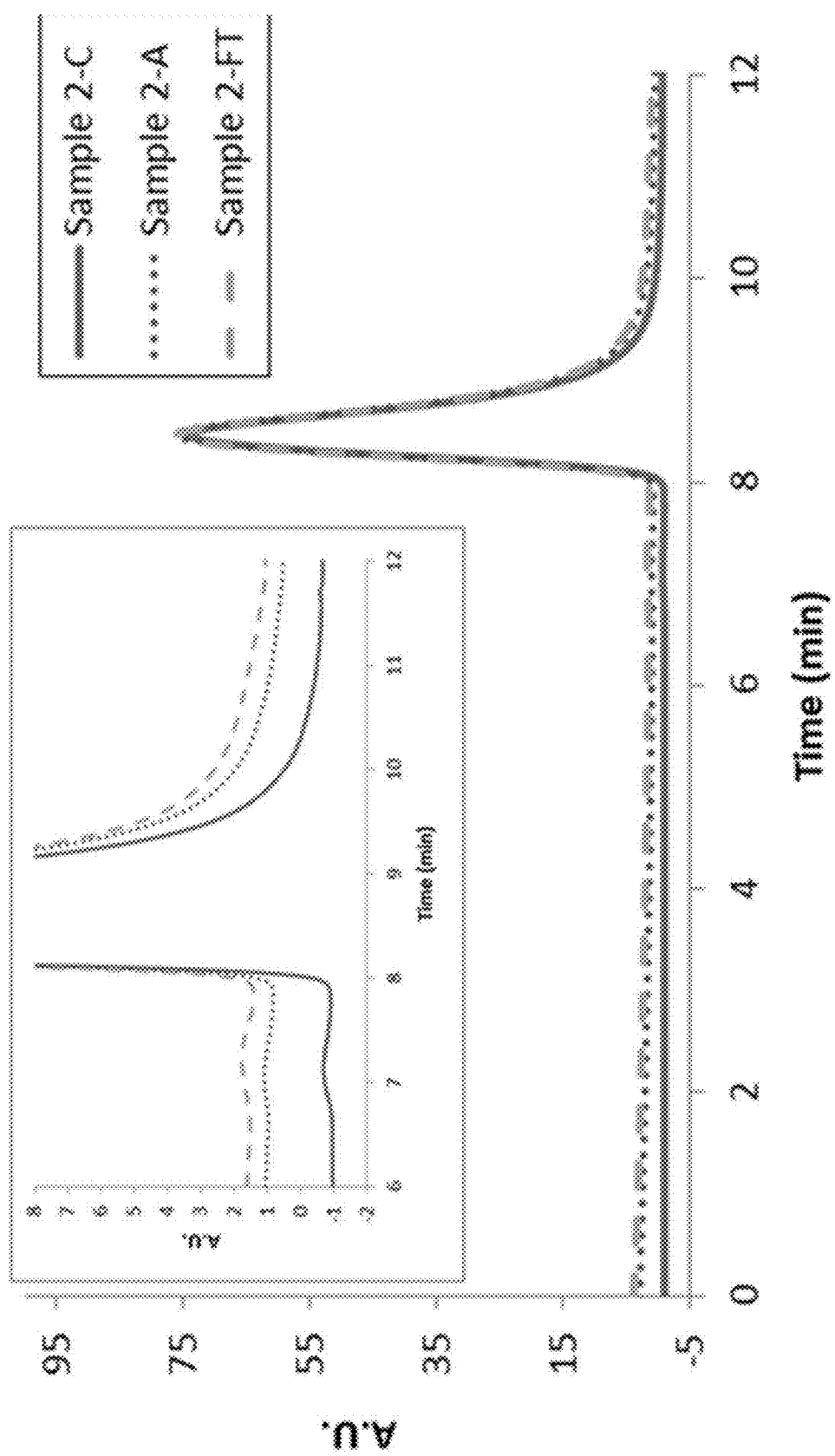
FIG. 3 shows a size exclusion chromatogram of monoclonal antibody solutions with a main monomer peak at 8-10 minutes retention time. The data curves in FIG. 3 have a baseline offset to allow comparison: the curves for Samples 2-C, 2-A, and 2-FT are offset in the Y-axis direction.

A Brookhaven Zeta Plus dynamic light scattering instrument was used to measure the hydrodynamic radius of the adalimumab molecules in the samples and to look for evidence of the formation of aggregate populations. Table 21 shows the DLS results for the 6 samples described in Table 20; some of them (1-A, 1-FT, 2-A, and 2-FT) had been exposed to stress conditions (stressed Samples), and others (1-C and 2-C) had not been stressed. In the absence of caffeine as an excipient, the stressed Samples 1-A and 1-FT showed higher effective diameter than non-stressed Sample 1-C and in addition they show a second population of particles of significantly higher diameter; this new grouping of particles with a larger diameter is evidence of aggregation into subvisible particles. The stressed samples containing the caffeine (Samples 2-A and 2-FT) only display one population at a particle diameter similar to the unstressed Sample 2-C. These results demonstrate the effect of adding caffeine to reduce or minimize the formation of aggregates or subvisible particles. Table 21 and FIGS. 1, 2, and 3 show the DLS data, where a multimodal particle size distribution of the monoclonal antibody is evident in stressed samples that do not contain caffeine.

TABLE 21

| Sample # | Effective Diameter (nm) | Diameter of Population #1 (nm) | % by Intensity of Population #1 | Diameter of Population #2 (nm) | % by Intensity of Population #2 |
|---|---|---|---|---|---|
| 1-C | 10.9 | 10.8 | 100 | — | — |
| 1-A | 11.5 | 10.8 | 87 | 28.9 | 13 |
| 1-FT | 20.4 | 11.5 | 66 | 112.2 | 44 |
| 2-C | 10.5 | 10.5 | 100 | — | — |
| 2-A | 10.8 | 10.8 | 100 | — | — |
| 2-FT | 11.4 | 11.4 | 100 | — | — |

Tables 22A and Table 22B display the DLS raw data of adalimumab samples showing the particle size distributions. G(d) is the intensity-weighted differential size distribution. C(d) is the cumulative intensity-weighted differential size distribution.

TABLE 22A

| Sample 1-C | | | Sample 1-A | | | Sample 1-FT | | |
|---|---|---|---|---|---|---|---|---|
| Diameter (nm) | G(d) | C(d) | Diameter (nm) | G(d) | C(d) | Diameter (nm) | G(d) | C(d) |
| 10.6 | 14 | 4 | 9.3 | 13 | 3 | 8.2 | 12 | 2 |
| 10.6 | 53 | 20 | 9.8 | 47 | 15 | 9.2 | 55 | 13 |
| 10.7 | 92 | 46 | 10.3 | 87 | 37 | 10.3 | 98 | 32 |
| 10.8 | 100 | 76 | 10.8 | 100 | 63 | 11.5 | 100 | 52 |
| 10.9 | 61 | 93 | 11.4 | 67 | 80 | 12.9 | 57 | 63 |
| 10.9 | 22 | 100 | 12 | 27 | 87 | 14.5 | 14 | 66 |
| | | | 26.1 | 4 | 88 | 89.3 | 5 | 67 |
| | | | 27.5 | 10 | 91 | 100.1 | 27 | 72 |
| | | | 28.9 | 13 | 94 | 112.2 | 52 | 83 |
| | | | 30.5 | 13 | 97 | 125.7 | 52 | 93 |
| | | | 32.1 | 7 | 99 | 140.8 | 30 | 99 |
| | | | 33.8 | 4 | 100 | 157.8 | 7 | 100 |

TABLE 22B

| Sample 2-C | | | Sample 2-A | | | Sample 2-FT | | |
|---|---|---|---|---|---|---|---|---|
| Diameter (nm) | G(d) | C(d) | Diameter (nm) | G(d) | C(d) | Diameter (nm) | G(d) | C(d) |
| 10.3 | 14 | 4 | 10.6 | 7 | 2 | 11.3 | 28 | 9 |
| 10.4 | 52 | 19 | 10.6 | 43 | 16 | 11.3 | 64 | 29 |
| 10.5 | 91 | 46 | 10.7 | 79 | 40 | 11.4 | 100 | 60 |
| 10.5 | 100 | 75 | 10.8 | 100 | 71 | 11.5 | 79 | 85 |
| 10.6 | 62 | 93 | 10.8 | 64 | 91 | 11.5 | 43 | 98 |
| 10.7 | 23 | 100 | 10.9 | 29 | 100 | 11.6 | 7 | 100 |

Example 29: Evaluation of Stability by Size-Exclusion Chromatography (SEC)

SEC was used to detect any subvisible particulates of less than about 0.1 microns in size from the stressed and unstressed adalimumab samples described above. A TSKgel SuperSW3000 column (Tosoh Biosciences, Montgomeryville, PA) with a guard column was used, and the elution was monitored at 280 nm. A total of 10 μl of each stressed and unstressed sample was eluted isocratically with a pH 6.2 buffer (100 mM phosphate, 325 mM NaCl), at a flow rate of 0.35 ml/min. The retention time of the adalimumab monomer was approximately 9 minutes. The data showed that samples containing caffeine as an excipient did not show any detectable aggregates. Also the amount of monomer in all 3 samples remained constant.

Example 30: Viscosity Reduction of HERCEPTIN®

The monoclonal antibody trastuzumab (HERCEPTIN® from Genentech) was received as a lyophilized powder and reconstituted to 21 mg/mL in DI water. The resulting solution was concentrated as-is in an Amicon Ultra 4 centrifugal concentrator tube (molecular weight cut-off, 30 KDa) by centrifuging at 3500 rpm for 1.5 hrs. The concentration was measured by diluting the sample 200 times in an appropriate buffer and measuring absorbance at 280 nm using the extinction coefficient of 1.48 mL/mg. Viscosity was measured using a RheoSense microVisc viscometer.

Excipient buffers were prepared containing salicylic acid and caffeine either alone or in combination by dissolving histidine and excipients in distilled water, then adjusting pH to the appropriate level. The conditions of Buffer Systems 1 and 2 are summarized in Table 23.

TABLE 23

| Buffer System # | Salicylic Acid concentration | Caffeine concentration | Osmolality (mOsm/kg) | pH |
|---|---|---|---|---|
| 1 | 10 mg/mL | 10 mg/mL | 145 | 6 |
| 2 | — | 15 mg/mL | 86 | 6 |

HERCEPTIN® solutions were diluted in the excipient buffers at a ratio of ~1:10 and concentrated in Amicon Ultra 15 (MWCO 30 KDa) concentrator tubes. Concentration was determined using a Bradford assay and compared with a standard calibration curve made from the stock HERCEPTIN® sample. Viscosity was measured using the RheoSense microVisc. The concentration and viscosity measurements of the various HERCEPTIN® solutions are shown in Table 24 below, where Buffer System 1 and 2 refer to those buffers identified in Table 23.

TABLE 24

| Control solution with no added excipients | | Solution with 10 mg/mL Caffeine + 10 mg/ml Salicylic Acid added (Buffer System 1) | | Solution with 15 mg/mL Caffeine added (Buffer System 2) | |
|---|---|---|---|---|---|
| Viscosity (cP) | Antibody Concentration (mg/mL) | Viscosity (cP) | Antibody Concentration (mg/mL) | Viscosity (cP) | Antibody Concentration (mg/mL) |
| 37.2 | 215 | 9.7 | 244 | 23.4 | 236 |
| 9.3 | 161 | 7.7 | 167 | 12.2 | 200 |
| 3.1 | 108 | 2.9 | 122 | 5.1 | 134 |
| 1.6 | 54 | 2.4 | 77 | 2.1 | 101 |

Buffer system 1, containing both salicylic acid and caffeine, had a maximum viscosity reduction of 76% at 215 mg/mL compared to the control sample. Buffer system 2, containing just caffeine, had viscosity reduction up to 59% at 200 mg/mL.

Example 31: Viscosity Reduction of AVASTIN®

AVASTIN® (bevacizumab formulation marketed by Genentech) was received as a 25 mg/ml solution in a histidine buffer. The sample was concentrated in Amicon Ultra 4 centrifugal concentrator tubes (MWCO 30 KDa) at 3500 rpm. Viscosity was measured by RheoSense microVisc and concentration was determined by absorbance at 280 nm (extinction coefficient, 1.605 mL/mg). The excipient buffer was prepared by adding 10 mg/mL caffeine along with 25 mM histidine HCl. AVASTIN® stock solution was diluted with the excipient buffer then concentrated in Amicon Ultra 15 centrifugal concentrator tubes (MWCO 30 KDa). The concentration of the excipient samples was determined by Bradford assay and the viscosity was measured using the RheoSense microVisc. Results are shown in Table 25 below.

TABLE 25

| Concentration (mg/mL) | Viscosity without added excipient (cP) | Viscosity with 10 mg/mL added caffeine excipient (cP) | % Viscosity Reduction from Excipient |
|---|---|---|---|
| 266 | 297 | 113 | 62% |
| 213 | 80 | 22 | 73% |
| 190 | 21 | 13 | 36% |

AVASTIN® showed a maximum viscosity reduction of 73% when concentrated with 10 mg/mL of caffeine to 213 mg/ml when compared to the control Avastin sample.

Example 32: Profile of HUMIRA®

HUMIRA® (AbbVie Inc., Chicago, IL) is a commercially available formulation of the therapeutic monoclonal antibody adalimumab, a TNF-alpha blocker typically prescribed to reduce inflammatory responses of autoimmune diseases such as rheumatoid arthritis, psoriatic arthritis, ankylosing spondylitis, Crohn's disease, ulcerative colitis, moderate to severe chronic psoriasis and juvenile idiopathic arthritis. HUMIRA® is sold in 0.8 mL single use doses containing 40 mg of adalimumab, 4.93 mg sodium chloride, 0.69 mg sodium phosphate monobasic dihydrate, 1.22 mg sodium phosphate dibasic dihydrate, 0.24 mg sodium citrate, 1.04 mg citric acid monohydrate, 9.6 mg mannitol and 0.8 mg polysorbate-80. A viscosity vs. concentration profile of this formulation was generated in the following way. An Amicon Ultra 15 centrifugal concentrator with a 30 kDa molecular weight cut-off (EMD-Millipore, Billerica, MA) was filled with about 15 mL of deionized water and centrifuged in a Sorvall Legend RT (Kendro Laboratory Products, Newtown, CT) at 4000 rpm for 10 minutes to rinse the membrane. Afterwards the residual water was removed and 2.4 mL of HUMIRA® liquid formulation was added to the concentrator tube and was centrifuged at 4000 rpm for 60 minutes at 25° C. Concentration of the retentate was determined by diluting 10 microliters of retentate with 1990 microliters of deionized water, measuring absorbance of the diluted sample at 280 nm, and calculating the concentration using the dilution factor and extinction coefficient of 1.39 mL/mg-cm. Viscosity of the concentrated sample was measured with a microVisc viscometer equipped with an A05 chip (RheoSense, San Ramon, CA) at a shear rate of 250 $sec^{-1}$ at 23° C. After viscosity measurement, the sample was diluted with a small amount of filtrate and concentration and viscosity measurements were repeated. This process was used to generate viscosity values at varying adalimumab concentrations as set forth in Table 26 below.

TABLE 26

| Adalimumab concentration (mg/mL) | Viscosity (cP) |
|---|---|
| 277 | 125 |
| 253 | 63 |
| 223 | 34 |
| 202 | 20 |
| 182 | 13 |

Example 33: Reformulation of HUMIRA® with Viscosity-Reducing Excipient

The following example describes a general process by which HUMIRA® was reformulated in buffer with viscosity-reducing excipient. A solution of the viscosity-reducing excipient was prepared in 20 mM histidine by dissolving about 0.15 g histidine (Sigma-Aldrich, St. Louis, MO) and 0.75 g caffeine (Sigma-Aldrich, St. Louis, MO) in deionized water. The pH of the resulting solution was adjusted to about 5 with 5 M hydrochloric acid. The solution was then diluted to a final volume of 50 mL in a volumetric flask with deionized water. The resulting buffered viscosity-reducing excipient solution was then used to reformulate HUMIRA® at high mAb concentrations. Next, about 0.8 mL of HUMIRA® was added to a rinsed Amicon Ultra 15 centrifugal concentrator tube with a 30 kDa molecular weight cutoff and centrifuged in a Sorvall Legend RT at 4000 rpm and 25° C. for 8-10 minutes. Afterwards about 14 mL of the buffered viscosity-reducing excipient solution prepared as described above was added to the concentrated HUMIRA® in the centrifugal concentrator. After gentle mixing, the sample was centrifuged at 4000 rpm and 25° C. for about 40-60 minutes. The retentate was a concentrated sample of HUMIRA® reformulated in a buffer with viscosity-reducing excipient. Viscosity and concentration of the sample were measured, and in some cases then diluted with a small amount of filtrate to measure viscosity at a lower concentration. Viscosity measurements were completed with a microVisc viscometer in the same way as with the concentrated HUMIRA® formulation in the previous example. Concentrations were determined with a Bradford assay using a standard curve generated from HUMIRA® stock solution diluted in deionized water. Reformulation of HUMIRA® with the viscosity-reducing excipient gave viscosity reductions of 30% to 60% compared to the viscosity values of HUMIRA® concentrated in the commercial buffer without reformulation, as set forth in Table 27 below.

TABLE 27

| Adalimumab concentration (mg/mL) | Viscosity (cP) |
|---|---|
| 290 | 61 |
| 273 | 48 |
| 244 | 20 |
| 205 | 14 |

Example 34: Preparation of Formulations Containing Caffeine, a Secondary Excipient and Test Protein Formulations were prepared using caffeine as the excipient compound or a combination of caffeine and a second excipient compound, and a test protein, where the test protein was intended to simulate a therapeutic protein that would be used in a therapeutic formulation. Such formulations were prepared in 20 mM histidine buffer with different excipient compounds for viscosity measurement in the following way. Excipient combinations (Excipients A and B, as described in Table 28 below) were dissolved in 20 mM histidine (Sigma-Aldrich, St. Louis, MO) and the resulting solution pH adjusted with small amounts of concentrated sodium hydroxide or hydrochloric acid to achieve pH 6 prior to dissolution of the model protein. Once excipient solutions had been prepared, the test protein (bovine gamma globulin (BGG) (Sigma-Aldrich, St. Louis, MO)) was dissolved at a ratio to achieve a final protein concentration of about 280 mg/mL. Solutions of BGG in the excipient solutions were formulated in 20 mL glass scintillation vials and allowed to shake at 80-100 rpm on an orbital shaker table overnight. The solutions were then transferred to 2 mL microcentrifuge tubes and centrifuged for about ten minutes at 2300 rpm in an IEC MicroMax microcentrifuge to remove entrained air prior to viscosity measurement.

Viscosity measurements of formulations prepared as described above were made with a DV-IIT LV cone and plate viscometer (Brookfield Engineering, Middleboro, MA). The viscometer was equipped with a CP-40 cone and was operated at 3 rpm and 25 degrees Centigrade. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty second measurement collection period. The three data points collected were then averaged and recorded as the viscosity for the sample. Viscosities of solutions with excipient were normalized to the viscosity of the model protein solution without excipient. The normalized viscosity is the ratio of the viscosity of the model protein solution with excipient to the viscosity of the model protein solution with no excipient.

TABLE 28

| Excipient A | | Excipient B | | |
|---|---|---|---|---|
| Name | Conc. (mg/mL) | Name | Conc. (mg/mL) | Normalized Viscosity |
| — | 0 | — | 0 | 1.00 |
| Caffeine | 15 | — | 0 | 0.77 |

TABLE 28-continued

| Excipient A | | Excipient B | | |
|---|---|---|---|---|
| Name | Conc. (mg/mL) | Name | Conc. (mg/mL) | Normalized Viscosity |
| Caffeine | 15 | Sodium acetate | 12 | 0.77 |
| Caffeine | 15 | Sodium sulfate | 14 | 0.78 |
| Caffeine | 15 | Aspartic acid | 20 | 0.73 |
| Caffeine | 15 | $CaCl_2$ dihydrate | 15 | 0.65 |
| Caffeine | 15 | Dimethyl Sulfone | 25 | 0.65 |
| Caffeine | 15 | Arginine | 20 | 0.63 |
| Caffeine | 15 | Leucine | 20 | 0.69 |
| Caffeine | 15 | Phenylalanine | 20 | 0.60 |
| Caffeine | 15 | Niacinamide | 15 | 0.63 |
| Caffeine | 15 | Ethanol | 22 | 0.65 |

Example 35: Preparation of Formulations Containing Dimethyl Sulfone and Test Protein Formulations were prepared using dimethyl sulfone (Jarrow Formulas, Los Angeles, CA) as the excipient compound and a test protein, where the test protein was intended to simulate a therapeutic protein that would be used in a therapeutic formulation. Such formulations were prepared in 20 mM histidine buffer for viscosity measurement in the following way. Dimethyl sulfone was dissolved in 20 mM histidine (Sigma-Aldrich, St. Louis, MO) and the resulting solution pH adjusted with small amounts of concentrated sodium hydroxide or hydrochloric acid to achieve pH 6 and then filtered through a 0.22 micron filter prior to dissolution of the model protein. Once excipient solutions had been prepared, the test protein (bovine gamma globulin (BGG) from Sigma-Aldrich, St. Louis, MO) was dissolved at a concentration of about 280 mg/mL. Solutions of BGG in the excipient solutions were formulated in 20 mL glass scintillation vials and allowed to shake at 80-100 rpm on an orbital shaker table overnight. The solutions were then transferred to 2 mL microcentrifuge tubes and centrifuged for about ten minutes at 2300 rpm in an IEC MicroMax microcentrifuge to remove entrained air prior to viscosity measurement.

Viscosity measurements of formulations prepared as described above were made with a DV-IIT LV cone and plate viscometer (Brookfield Engineering, Middleboro, MA). The viscometer was equipped with a CP-40 cone and was operated at 3 rpm and 25 degrees Centigrade. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty second measurement collection period. The three data points collected were then averaged and recorded as the viscosity for the sample. Viscosities of solutions with excipient were normalized to the viscosity of the model protein solution without excipient. The normalized viscosity is the ratio of the viscosity of the model protein solution with excipient to the viscosity of the model protein solution with no excipient.

TABLE 29

| Dimethyl sulfone concentration (mg/mL) | Normalized viscosity |
|---|---|
| 0 | 1.00 |
| 15 | 0.92 |
| 30 | 0.71 |
| 50 | 0.71 |
| 30 | 0.72 |

Example 36: Preparation of Formulations Containing Tannic Acid

In this Example, a high molecular weight poly(ethylene oxide) (PEG) molecule is used as a model compound to mimic the viscosity behavior of a PEGylated protein. A control sample (#36.1 in Table 30) was prepared by mixing PEG (Sigma-Aldrich, Saint Louis, MO) with viscosity averaged molecular weight (MV) of 1,000,000 with deionized (DI) water to make approximately 1.8% by weight PEG solution in sterile 5 mL polypropylene centrifuge tubes. Two samples, #36.2 and 36.3, with tannic acid (TA, Spectrum Chemicals, New Brunswick, NJ) were prepared with TA:PEG mass ratios of approximately 1:100 and 1:1000 respectively by mixing the appropriate amounts PEG, TA, and 1 mM KCl prepared in DI water. All samples were placed on a Daigger Scientific (Vernon Hills, IL) Labgenius orbital shaker at 200 rpm overnight. Viscosity measurements were made on a microVISC rheometer (RheoSense, San Ramon, CA) at 20° C. and a wall shear rate of 250 $s^{-1}$. After measurement, the viscosities were normalized to the respective PEG concentrations to account for the concentration dependence of the viscosity. The PEG concentrations, TA concentrations, viscosities, normalized viscosities, and viscosity reductions for the samples 36.1, 36.2, and 36.3 are listed in Table 30 below. The addition of TA to concentrated PEG solutions substantially decreases the solution viscosity by up to approximately 40%.

TABLE 30

| Sample | PEG concentration (wt. %) | TA concentration (wt. %) | Viscosity (cP) | Normalized viscosity (Viscosity/wt. % PEG) | % Reduction in normalized viscosity from control |
|---|---|---|---|---|---|
| 36.1 | 1.79 | 0 | 128 | 71.4 | N/A |
| 36.2 | 1.79 | $1.78 \times 10^{-2}$ | 75.0 | 41.9 | 41.3 |
| 36.3 | 1.80 | $1.71 \times 10^{-3}$ | 84.5 | 46.9 | 34.3 |

Example 37: Formulations with Excipient Dose Profile

Formulations were prepared with different molar concentrations of excipient and a test protein, where the test protein was intended to simulate a therapeutic protein that would be used in a therapeutic formulation. Such formulations were prepared in 20 mM histidine buffer for viscosity measurement in the following way. Stock solutions of 0 and 80 mM caffeine excipient were prepared in 20 mM histidine (Sigma-Aldrich, St. Louis, MO) and the resulting solution pH adjusted with small amounts of concentrated sodium hydroxide or hydrochloric acid to achieve pH 6 prior to dissolution of the model protein. Additional solutions at various caffeine concentrations were prepared by blending the two stock solutions at various volume ratios. Once excipient solutions had been prepared, the test protein (bovine gamma globulin (BGG, Sigma-Aldrich, St. Louis, MO)) was dissolved at a ratio to achieve a final protein concentration of about 280 mg/mL by adding 0.7 mL solution to 0.25 g lyophilized protein powder. Solutions of BGG in the excipient solutions were formulated in 5 mL sterile polypropylene tubes and allowed to shake at 100 rpm on an orbital shaker table overnight to dissolve. The solutions were then transferred to 2 mL microcentrifuge tubes and centrifuged for five minutes at 2400 rpm in an IEC MicroMax microcentrifuge to remove entrained air prior to viscosity measurement.

Viscosity measurements of formulations prepared as described above were made with a microVisc viscometer (RheoSense, San Ramon, CA). The viscometer was equipped with an A-10 chip having a channel depth of 100 microns, and was operated at a shear rate of 250 s$^{-1}$ and 25 degrees Centigrade. To measure viscosity, the formulation was loaded into the viscometer, taking care to remove all air bubbles from the pipette. The pipette with the loaded sample formulation was placed in the instrument and allowed to incubate at the measurement temperature for five minutes. The instrument was then run until the channel was fully equilibrated with the test fluid, indicated by a stable viscosity reading, and then the viscosity recorded in centipoise. The results of these measurements are listed in Table 31.

TABLE 31

| Test # | Excipient conc. (mM) | Excipient conc. (mg/mL) | Viscosity (cP) | Normalized Viscosity |
|---|---|---|---|---|
| 37.1 | 20 | 3.9 | 77 | 0.92 |
| 37.2 | 50 | 9.7 | 65 | 0.78 |
| 37.3 | 10 | 1.9 | 70 | 0.84 |
| 37.4 | 5 | 1.0 | 67 | 0.81 |
| 37.5 | 30 | 5.8 | 63 | 0.76 |
| 37.6 | 40 | 7.8 | 65 | 0.78 |
| 37.7 | 0 | 0.0 | 83 | 1.00 |
| 37.8 | 70 | 13.6 | 50 | 0.60 |
| 37.9 | 80 | 15.5 | 50 | 0.60 |
| 37.10 | 60 | 11.7 | 57 | 0.69 |

Example 38: Preparation of Formulations Containing Phenolic Compounds

In this Example, a high molecular weight poly(ethylene oxide) (PEG) molecule is used as a model compound to mimic the viscosity behavior of a PEGylated protein. A control sample was prepared by mixing PEG (Sigma-Aldrich, Saint Louis, MO) with a viscosity averaged molecular weight (MV) of 1,000,000 with deionized (DI) water to approximately 1.8% by weight PEG in sterile 5 mL polypropylene centrifuge tubes. The phenolic compounds gallic acid (GA, Sigma-Aldrich, Saint Louis, MO), pyrogallol (PG, Sigma-Aldrich, Saint Louis, MO) and resorcinol (R, Sigma-Aldrich, Saint Louis, MO) were tested as excipients as follows. Three PEG containing samples were prepared with added GA, PG and R at excipient:PEG mass ratios of approximately 3:50, 1:2, and 1:2 respectively by mixing the appropriate amounts PEG, excipient, and DI water. Samples were placed on a Daigger Scientific (Vernon Hills, IL) Labgenius orbital shaker at 200 rpm overnight. Viscosity measurements were made on a microVISC rheometer (RheoSense, San Ramon, CA) at 20° C. and a wall shear rate of 250 s$^{-1}$. After measurement, the viscosities were normalized to the respective PEG concentrations to account for the concentration dependence of the viscosity. The PEG concentrations, excipient concentrations, viscosities, normalized viscosities, and viscosity reductions for the control and excipient-containing samples are listed in Table 32 below.

TABLE 32

| Sample # | PEG conc. (wt. %) | Excipient added | Excipient conc. (wt. %) | Viscosity (cP) | Normalized viscosity (Viscosity/ wt. % PEG) | % Reduction in normalized viscosity from control |
|---|---|---|---|---|---|---|
| 38.1 | 1.80 | None | 0.000 | 134 | 74.5 | N/A |
| 38.2 | 1.80 | GA | 0.206 | 120 | 67.0 | 10.1 |
| 38.3 | 1.80 | PG | 0.870 | 106 | 59.2 | 19.6 |
| 38.4 | 1.80 | R | 1.00 | 113 | 63.1 | 15.3 |

Example 39: Preparation of Formulations Containing Excipients Having a Pyrimidine Ring and Test Protein Formulations were prepared using an excipient compound having a structure that included one pyrimidine ring and a test protein, where the test protein was intended to simulate a therapeutic protein that would be used in a therapeutic formulation. Such formulations were prepared in 20 mM histidine buffer with different excipient compounds in the following way. Excipient compounds as listed in Table 33 were dissolved in an aqueous solution of 20 mM histidine (Sigma-Aldrich, St. Louis, MO) and the resulting solution pH was adjusted with small amounts of concentrated sodium hydroxide or hydrochloric acid to achieve pH 6 prior to dissolution of the model protein. Once the excipient solutions had been prepared, the test protein (bovine gamma globulin (BGG, Sigma-Aldrich, St. Louis, MO)) was dissolved in each at a ratio to achieve a final protein concentration of 280 mg/mL. Solutions of BGG in the excipient solutions were formulated in 20 mL glass scintillation vials and agitated at 100 rpm on an orbital shaker table overnight. The solutions were then transferred to 2 mL microcentrifuge tubes and centrifuged for ten minutes at 2300 rpm in an IEC MicroMax microcentrifuge to remove entrained air prior to viscosity measurement.

Viscosity measurements of formulations prepared as described above were made with a DV-III LV cone and plate viscometer (Brookfield Engineering, Middleboro, MA). The viscometer was equipped with a CP-40 cone and was operated at 3 rpm and 25 degrees Centigrade. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty second measurement collection period. The three data points collected were then averaged and recorded as the viscosity for the sample. Viscosities of solutions with excipient were normalized to the viscosity of the model protein solution without excipient. The normalized viscosity is the ratio of the viscosity of the model protein solution with excipient to the viscosity of the model protein solution with no excipient. Results of these tests are shown in Table 33.

TABLE 33

| Sample # | Excipient Added | Excipient MW (g/mol) | Excipient Conc (mg/mL) | Normalized Viscosity |
|---|---|---|---|---|
| 39.1 | Pyrimidinone | 96.1 | 14 | 0.73 |
| 39.2 | 1,3-Dimethyluracil | 140.1 | 22 | 0.67 |
| 39.3 | Triaminopyrimidine | 125.1 | 20 | 0.87 |
| 39.4 | Caffeine | 194 | 15 | 0.77 |
| 39.5 | Pyrimidinone | 96.1 | 7 | 0.82 |
| 39.6 | 1,3-Dimethyluracil | 140.1 | 11 | 0.76 |
| 39.7 | Pyrimidine | 80.1 | 13 | 0.78 |
| 39.8 | Pyrimidine | 80.1 | 6.5 | 0.87 |
| 39.9 | None | n/a | 0 | 0.97 |
| 39.10 | None | n/a | 0 | 1.00 |
| 39.11 | None | n/a | 0 | 0.95 |
| 39.12 | Theacrine | 224 | 15 | 0.73 |
| 39.13 | Theacrine | 224 | 15 | 0.77 |

EQUIVALENTS

While specific embodiments of the subject invention have been disclosed herein, the above specification is illustrative and not restrictive. While this invention has been particularly shown and described with references to preferred embodiments thereof, it will be understood by those skilled in the art that various changes in form and details may be made therein without departing from the scope of the invention encompassed by the appended claims. Many variations of the invention will become apparent to those of skilled art upon review of this specification. Unless otherwise indicated, all numbers expressing reaction conditions, quantities of ingredients, and so forth, as used in this specification and the claims are to be understood as being modified in all instances by the term "about." Accordingly, unless indicated to the contrary, the numerical parameters set forth herein are approximations that can vary depending upon the desired properties sought to be obtained by the present invention.

What is claimed is:

1. An injectable liquid pharmaceutical formulation comprising:
   a) at least about 10 mg/ml therapeutic antibody;
   b) a viscosity reducing amount of caffeine, wherein the viscosity reducing amount of caffeine is 2% or less by weight of the injectable liquid pharmaceutical formulation; and
   c) a viscosity reducing amount of an aromatic acid, wherein viscosity of the injectable liquid pharmaceutical formulation is less than about 100 cP.

2. The injectable liquid pharmaceutical formulation of claim 1, wherein the aromatic acid is salicylic acid.

3. The injectable liquid pharmaceutical formulation of claim 1, wherein the aromatic acid is nicotinic acid.

4. The injectable liquid pharmaceutical formulation of claim 3, wherein the aromatic acid is nicotinic acid sodium salt.

5. The injectable liquid pharmaceutical formulation of claim 1, wherein the viscosity reducing amount of caffeine is less than about 20 mg/ml.

6. The injectable liquid pharmaceutical formulation of claim 1, wherein the injectable liquid pharmaceutical formulation further comprises a buffer.

7. The injectable liquid pharmaceutical formulation of claim 6, wherein the buffer is a histidine buffer.

8. The injectable liquid pharmaceutical formulation of claim 6, wherein the buffer is a phosphate buffer.

9. The injectable liquid pharmaceutical formulation of claim 1, wherein the therapeutic antibody is selected from the group consisting of bevacizumab, trastuzumab, adalimumab, infliximab, etanercept, darbepoetin alfa, epoetin alfa, cetuximab, pegfilgrastim, filgrastim, and rituximab.

10. The injectable liquid pharmaceutical formulation of claim 1, wherein the viscosity of the injectable liquid pharmaceutical formulation is less than about 50 cP.

11. The injectable liquid pharmaceutical formulation of claim 1, wherein the injectable liquid pharmaceutical formulation contains at least about 100 mg/mL of the therapeutic antibody.

12. The injectable liquid pharmaceutical formulation of claim 1, wherein the injectable liquid pharmaceutical formulation contains at least about 200 mg/mL of the therapeutic antibody.

13. An injectable liquid pharmaceutical formulation comprising:
   a) at least about 10 mg/ml therapeutic antibody; and
   b) a viscosity reducing amount of nicotinic acid, wherein viscosity of the injectable liquid pharmaceutical formulation is less than about 100 cP and the viscosity reducing amount of nicotinic acid is at least 8% by weight of the injectable liquid pharmaceutical formulation.

14. The injectable liquid pharmaceutical formulation of claim 13, wherein the nicotinic acid is nicotinic acid sodium salt.

15. The injectable liquid pharmaceutical formulation of claim 13, wherein the injectable liquid pharmaceutical formulation further comprises a hindered amine.

16. The injectable liquid pharmaceutical formulation of claim 13, wherein the injectable liquid pharmaceutical formulation further comprises a buffer.

17. The injectable liquid pharmaceutical formulation of claim 16, wherein the buffer is a histidine buffer.

18. The injectable liquid pharmaceutical formulation of claim 16, wherein the buffer is a phosphate buffer.

19. The injectable liquid pharmaceutical formulation of claim 13, wherein the therapeutic antibody is selected from the group consisting of bevacizumab, trastuzumab, adalimumab, infliximab, etanercept, darbepoetin alfa, epoetin alfa, cetuximab, pegfilgrastim, filgrastim, and rituximab.

20. The injectable liquid pharmaceutical formulation of claim 13, wherein the viscosity of the injectable liquid pharmaceutical formulation is less than about 50 cP.

21. The injectable liquid pharmaceutical formulation of claim 13, wherein the injectable liquid pharmaceutical formulation contains at least about 100 mg/mL of the therapeutic antibody.

22. The injectable liquid pharmaceutical formulation of claim 13, wherein the injectable liquid pharmaceutical formulation contains at least about 200 mg/mL of the therapeutic antibody.

23. The injectable liquid pharmaceutical formulation of claim 1, wherein the therapeutic antibody is gamma globulin.

24. The injectable liquid pharmaceutical formulation of claim 1, wherein the viscosity reducing amount of caffeine is about 15 mg/ml or less.

25. The injectable liquid pharmaceutical formulation of claim 13, wherein the viscosity reducing amount of nicotinic acid is less than 300 mg/ml.

\* \* \* \* \*